(12) United States Patent
Keusenkothen et al.

(10) Patent No.: US 9,815,751 B2
(45) Date of Patent: Nov. 14, 2017

(54) HYDROCARBON AND OXYGENATE CONVERSION BY HIGH SEVERITY PYROLYSIS TO MAKE ACETYLENE AND ETHYLENE

(75) Inventors: Paul F. Keusenkothen, Houston, TX (US); Frank Hershkowitz, Basking Ridge, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 630 days.

(21) Appl. No.: 13/993,211

(22) PCT Filed: Dec. 20, 2011

(86) PCT No.: PCT/US2011/066180
§ 371 (c)(1),
(2), (4) Date: Sep. 18, 2013

(87) PCT Pub. No.: WO2012/099674
PCT Pub. Date: Jul. 26, 2012

(65) Prior Publication Data
US 2014/0163271 A1    Jun. 12, 2014

Related U.S. Application Data

(60) Provisional application No. 61/434,410, filed on Jan. 19, 2011, provisional application No. 61/434,415, (Continued)

(30) Foreign Application Priority Data

Jun. 24, 2011 (EP) .................................... 11171344

(51) Int. Cl.
*C07C 5/05* (2006.01)
*C07C 2/84* (2006.01)
(Continued)

(52) U.S. Cl.
CPC .................. *C07C 5/05* (2013.01); *C07C 2/84* (2013.01); *C10G 3/00* (2013.01); *C10G 9/00* (2013.01);
(Continued)

(58) Field of Classification Search
CPC ............ C07C 2/74–2/86; C07C 2/862; C07C 1/00–1/02; C07C 4/00; C07C 4/02;
(Continued)

(56) References Cited

U.S. PATENT DOCUMENTS 1,134,677 A    4/1915    Heinemann
1,860,624 A    5/1932    Sauerwein
(Continued)

FOREIGN PATENT DOCUMENTS

BE    722895    10/1968
DE    875198    4/1953
(Continued)

OTHER PUBLICATIONS

Mohundro , "Overview on C2 and C3 Selective Hydrogenation in Ethylene Plants", AIChE Presentation, Apr. 2003, pg. 531-560.*
(Continued)

*Primary Examiner* — In Suk Bullock
*Assistant Examiner* — Ali Z Fadhel

(57) ABSTRACT

The invention relates to hydrocarbon conversion processes, e.g., to processes for producing acetylene from hydrocarbon and then hydrogenating at least a portion of the acetylene. The invention also relates to polymerizing one or more products derived from the acetylene saturation, and to equipment useful for these processes.

21 Claims, 4 Drawing Sheets

Related U.S. Application Data filed on Jan. 19, 2011, provisional application No. 61/434,417, filed on Jan. 19, 2011, provisional application No. 61/434,419, filed on Jan. 19, 2011, provisional application No. 61/434,409, filed on Jan. 19, 2011, provisional application No. 61/434,413, filed on Jan. 19, 2011, provisional application No. 61/434,411, filed on Jan. 19, 2011, provisional application No. 61/481,999, filed on May 3, 2011, provisional application No. 61/500,854, filed on Jun. 24, 2011, provisional application No. 61/504,611, filed on Jul. 5, 2011.

(51) Int. Cl.

| | | |
|---|---|---|
| C10G 45/32 | (2006.01) | |
| C10G 57/00 | (2006.01) | |
| C10G 69/06 | (2006.01) | |
| C10G 70/02 | (2006.01) | |
| C10G 3/00 | (2006.01) | |
| C10G 9/00 | (2006.01) | |

(52) U.S. Cl.
CPC .......... *C10G 45/32* (2013.01); *C10G 57/00* (2013.01); *C10G 69/06* (2013.01); *C10G 70/02* (2013.01); *Y02P 30/20* (2015.11)

(58) Field of Classification Search
CPC .......... C07C 4/025; C07C 4/04; C10G 69/00; C10G 69/02; C10G 69/06; C10G 2/31
See application file for complete search history.

(56) References Cited

U.S. PATENT DOCUMENTS

| | | | |
|---|---|---|---|
| 2,319,679 A | | 5/1943 | Hasche et al. |
| 2,678,339 A | | 5/1954 | Harris |
| 2,692,819 A | | 10/1954 | Hasche et al. |
| 3,024,094 A | | 3/1962 | Coberly |
| 3,093,697 A | | 6/1963 | Kasbohm et al. |
| 3,156,733 A | | 11/1964 | Happel et al. |
| 3,242,223 A | | 3/1966 | Nonnenmacher et al. |
| 3,419,632 A | | 12/1968 | Sogawa et al. |
| 3,617,495 A | | 11/1971 | Zimmerman, Jr. et al. |
| 3,644,555 A | | 2/1972 | Nagy et al. |
| 3,676,516 A | * | 7/1972 | Haskell et al. .......... C07C 7/148 |
| | | | 423/230 |
| 3,839,484 A | | 10/1974 | Zimmerman, Jr. et al. |
| 4,274,841 A | | 6/1981 | Andresen et al. |
| 4,705,906 A | * | 11/1987 | Brophy et al. ............ C07C 5/09 |
| | | | 585/260 |
| 5,675,041 A | | 10/1997 | Kiss et al. |
| 5,804,689 A | * | 9/1998 | Schodel et al. .......... C07C 4/04 |
| | | | 585/539 |
| 5,824,834 A | * | 10/1998 | Bachtler et al. .......... C01B 3/36 |
| | | | 585/537 |
| 5,856,592 A | | 1/1999 | Hagen |
| 6,049,011 A | | 4/2000 | Kiss et al. |
| 6,121,503 A | | 9/2000 | Janssen et al. |
| 6,177,600 B1 | | 1/2001 | Netzer |
| 6,210,561 B1 | | 4/2001 | Bradow et al. |
| 6,307,093 B1 | | 10/2001 | Godwin et al. |
| 6,578,378 B2 | | 6/2003 | Kaiser et al. |
| 7,045,670 B2 | | 5/2006 | Johnson et al. |
| 7,115,789 B2 | | 10/2006 | Kuechler et al. |
| 7,119,240 B2 | | 10/2006 | Hall et al. |
| 7,138,047 B2 | | 11/2006 | Stell et al. |
| 7,208,647 B2 | | 4/2007 | Peterson et al. |
| 7,491,250 B2 | | 2/2009 | Hershkowitz et al. |
| 7,815,873 B2 | | 10/2010 | Sankaranarayanan et al. |
| 7,846,401 B2 | | 12/2010 | Hershkowitz et al. |
| 7,943,808 B2 | | 5/2011 | Hershkowitz et al. |
| 8,158,837 B2 | | 4/2012 | Mamadov et al. |
| 8,440,070 B2 | | 5/2013 | Keusenkothen |
| 9,346,728 B2 | | 5/2016 | Keusenkothen et al. |
| 2002/0000085 A1 | | 1/2002 | Hall et al. |
| 2002/0098430 A1 | | 7/2002 | Kawamura et al. |
| 2004/0002553 A1 | | 1/2004 | Hall et al. |
| 2004/0192982 A1 | | 9/2004 | Kuechler et al. |
| 2004/0267079 A1 | * | 12/2004 | Mamedov et al. ........ C01B 3/38 |
| | | | 585/400 |
| 2005/0049445 A1 | * | 3/2005 | Johnson et al. ......... B01J 23/50 |
| | | | 585/258 |
| 2007/0006732 A1 | * | 1/2007 | Mitariten ........... B01D 53/0462 |
| | | | 95/237 |
| 2007/0090018 A1 | | 4/2007 | Keusenkothen et al. |
| 2007/0090019 A1 | | 4/2007 | Keusenkothen et al. |
| 2007/0090020 A1 | | 4/2007 | Buchanan et al. |
| 2007/0144940 A1 | | 6/2007 | Hershkowitz et al. |
| 2007/0191664 A1 | * | 8/2007 | Hershkowitz et al. ... B01F 3/02 |
| | | | 585/539 |
| 2008/0142049 A1 | | 6/2008 | Onishi et al. |
| 2008/0142409 A1 | | 6/2008 | Sankaranarayanan et al. |
| 2008/0300438 A1 | | 12/2008 | Keusenkothen et al. |
| 2010/0130803 A1 | | 5/2010 | Keusenkothen et al. |
| 2010/0234476 A1 | * | 9/2010 | Lin et al. .................. C07C 2/78 |
| | | | 518/702 |
| 2010/0292523 A1 | | 11/2010 | Hershkowitz et al. |
| 2011/0054231 A1 | * | 3/2011 | Peterson .................. C07C 2/78 |
| | | | 585/251 |

FOREIGN PATENT DOCUMENTS

| | | |
|---|---|---|
| DE | 1270537 | 6/1968 |
| DE | 2354217 | 5/1975 |
| EP | 0070690 A1 * | 1/1983 |
| EP | 1288182 | 3/2003 |
| EP | 1741691 | 1/2007 |
| EP | 2022772 | 2/2009 |
| EP | 2022772 A1 * | 2/2009 |
| GB | 795688 | 5/1958 |
| GB | 834419 | 5/1960 |
| GB | 846679 | 8/1960 |
| GB | 1007423 | 10/1965 |
| GB | 1090983 | 11/1967 |
| WO | 2005/097948 | 10/2005 |
| WO | 2011/008389 | 1/2011 |
| WO | 2012/099679 | 7/2012 |

OTHER PUBLICATIONS

Energy Fuels, 2007, 21(2), pp. 640-645.
Watt, L., "The Production of Acetlene from Methane by Partial Oxidation", Thesis University Og British Columbia, Sep. 1, 1951, pp. 1-50.
Sri Consulting Process Economics Program "Acetylene" Report 16 (1966) and 16A (1982).
U.S. Appl. No. 61/349,464, Hershkowitz et al., filed May 28, 2010.

* cited by examiner

HYDROCARBON AND OXYGENATE CONVERSION BY HIGH SEVERITY PYROLYSIS TO MAKE ACETYLENE AND ETHYLENE

CROSS-REFERENCE OF RELATED APPLICATIONS

This application claims priority from (i) U.S. Provisional Application Ser. No. 61/481,999, filed May 3, 2011, EP Application No. 11171344.2, filed Jun. 24, 2011, and PCT/US2011/066180, filed Dec. 20, 2011; (ii) U.S. Provisional Application Ser. No. 61/434,409, filed Jan. 19, 2011, and PCT/US2011/066216, filed Dec. 20, 2011; (iii) U.S. Provisional Application Ser. No. 61/434,410, filed Jan. 19, 2011, and PCT/US2011/066202, filed Dec. 20, 2011; (iv) U.S. Provisional Application Ser. No. 61/434,411, filed Jan. 19, 2011, and PCT/US2011/066210, filed Dec. 20, 2011; (v) U.S. Provisional Application Ser. No. 61/434,413, filed Jan. 19, 2011, and PCT/US2011/066196, filed Dec. 20, 2011; (vi) U.S. Provisional Application Ser. No. 61/434,415, filed Jan. 19, 2011, and PCT/US2011/066152, filed Dec. 20, 2011; (vii) U.S. Provisional Application Ser. No. 61/434,417, filed Jan. 19, 2011, and PCT/US2011/066186, filed Dec. 20, 2011; (viii) U.S. Provisional Application Ser. No. 61/434,419, filed Jan. 19, 2011, and PCT/US2011/066206, filed Dec. 20, 2011; (ix) U.S. Provisional Application Ser. No. 61/500,854, filed Jun. 24, 2011, and PCT/US2011/066174, filed Dec. 20, 2011; and (x) U.S. Provisional Application Ser. No. 61/504,611, filed Jul. 5, 2011, and PCT/US2011/066165, filed Dec. 20, 2011, the contents of each of which are incorporated by reference in their entirety.

FIELD

The invention relates to hydrocarbon conversion processes, e.g., to processes for producing acetylene from hydrocarbon and then hydrogenating at least a portion of the acetylene. The invention also relates to polymerizing one or more products derived from the acetylene saturation, and to equipment useful for these processes.

BACKGROUND

Olefins such as ethylene are commonly used for producing polymers such as polyolefin. Ethylene can be produced in conventional processes such as steam cracking, but such processes also produce acetylene. Since acetylene is a poison for many polymerization catalysts, it is generally converted to ethylene before polymerization occurs. Other hydrocarbon conversion processes, such as partial oxidation, can produce an even greater amount of acetylene in their $C_2$ unsaturate product.

Acetylene can be converted to ethylene using, e.g., acetylene conversion catalysts such as those containing one or more elements from Group VIII of the Periodic Table. One important consideration in acetylene conversion is the relative amounts of ethylene and ethane produced in the conversion. It has been observed that the selectivity for ethylene production (instead of ethane) can be increased when the catalyst is exposed to carbon monoxide in an amount in the range of about 10.0 ppm to about $1.0 \times 10^4$ ppm per mole of feed. Since steam cracking of hydrocarbon feeds generally results in the production of little if any carbon monoxide, acetylene conversion processes downstream of steam cracking reactors generally employ an external carbon monoxide source, which undesirably increases process complexity.

Conventional partial oxidation processes for making acetylene produce carbon monoxide in addition to $C_2$ unsaturates, but the carbon monoxide amount is so large as to be a poison for the acetylene conversion catalyst.

There is therefore a need for a hydrocarbon conversion process that produces acetylene and an amount of carbon monoxide that is suitable for increasing the selectivity of acetylene conversion catalysts.

SUMMARY

In an embodiment, the invention relates to a hydrocarbon conversion process, comprising:
(a) providing a first mixture, the first mixture comprising hydrocarbon and oxygenate;
(b) exposing the first mixture to a temperature $\geq 1400°$ C. in a first region under pyrolysis conditions to form a second mixture, the second mixture having a carbon monoxide to acetylene molar ratio in the range of $2.5 \times 10^{-3}$ to 3.0 and comprising $\geq 1.0$ wt. % $C_2$ unsaturates based on the weight of the second mixture;
(c) transferring to at least one acetylene converter at least one of (i) at least a portion of the second mixture or (ii) a third mixture derived from the second mixture, the transferred mixture having a carbon monoxide to acetylene molar ratio in the range of 0.01 to 1.5 and comprising $A_2$ wt. % of acetylene and $A_3$ wt. % of ethylene based on the weight of the third mixture; and
(d) converting at least a portion of the transferred mixture to form a product, the product comprising $A_2$ wt. % of acetylene and $A_6$ wt. % of ethylene based on the weight of the product; and wherein $A_6 \geq A_3$, $A_5 < A_2$, and $(A_6 - A_3)/(A_2 - A_5) \geq 0.50$.

In another embodiment, the invention relates to a hydrocarbon conversion process, comprising:
(a) providing a first mixture, the first mixture comprising hydrocarbon and an oxygenate, wherein (i) the first mixture has an O:C atomic ratio in the range of $4.0 \times 10^{-4}$ to $1.0 \times 10^{-1}$ and the (ii) oxygenate has an Effectiveness Factor $\geq 0.4$;
(b) exposing the first mixture to a temperature $\geq 1400°$ C. under high-severity, thermal pyrolysis conditions to form a second mixture, wherein (i) the second mixture comprises $\geq 1.0$ wt. % $C_2$ unsaturates, $A_1$ wt. % of saturated hydrocarbon, $A_2$ wt. % of acetylene, and $A_3$ wt. % of ethylene based on the weight of the second mixture and (ii) the second mixture has a carbon monoxide to acetylene molar ratio in the range of 0.04 to 0.50; and (c) catalytically converting at least a portion of the second mixture to form a product, the product comprising $A_4$ wt. % of saturated hydrocarbon, $A_5$ wt. % of acetylene, and $A_6$ wt. % of ethylene based on the weight of the product; wherein (i) $A_6 \geq A_3$, (ii) $A_5 < A_2$, (iii) $(A_6 - A_3)/(A_2 - A_5) \geq 0.70$, and (iv) the conversion catalyst is selectivated by at least a portion of the second mixture's carbon monoxide.

In yet another embodiment, the invention relates to a hydrocarbon conversion process, comprising:
(a) providing a first mixture, the first mixture comprising hydrocarbon and an oxygenate, wherein (i) the first mixture has an O:C atomic ratio in the range of $4.0 \times 10^{-4}$ to $1.0 \times 10^{-1}$ and the (ii) oxygenate has an Effectiveness Factor $\geq 0.4$;
(b) exposing the first mixture to a temperature $\geq 1400°$ C. under high-severity, thermal pyrolysis conditions to form a second mixture, the second mixture having a carbon monoxide to acetylene molar ratio in the range of 2.5×

$10^{-3}$ to 3.0 and comprising ≥1.0 wt. % $C_2$ unsaturates based on the weight of the second mixture;
(c) deriving a third mixture from the second mixture, wherein (i) the third mixture comprises ≥1.0 wt. % $C_2$ unsaturates, $A_1$ wt. % of saturated hydrocarbon, $A_2$ wt. % of acetylene, and $A_3$ wt. % of ethylene based on the weight of the second mixture and (ii) the third mixture has a carbon monoxide to acetylene molar ratio in the range of 0.04 to 0.50; and
(d) catalytically converting at least a portion of the third mixture to form a product, the product comprising $A_4$ wt. % of saturated hydrocarbon, $A_5$ wt. % of acetylene, and $A_6$ wt. % of ethylene based on the weight of the product; wherein (i) $A_6 \geq A_3$, (ii) $A_5 < A_2$, (iii) $(A_6-A_3)/(A_2-A_5) \geq 0.70$ and (iv) the conversion catalyst is selectivated by at least a portion of the third mixture's carbon monoxide.

BRIEF DESCRIPTION OF THE DRAWINGS

In FIGS. 1, 2A, 2B, 3A, and 3B, stages and components serving the same function are identified by the same reference numbers.

DETAILED DESCRIPTION OF THE EMBODIMENTS

Figure 1:
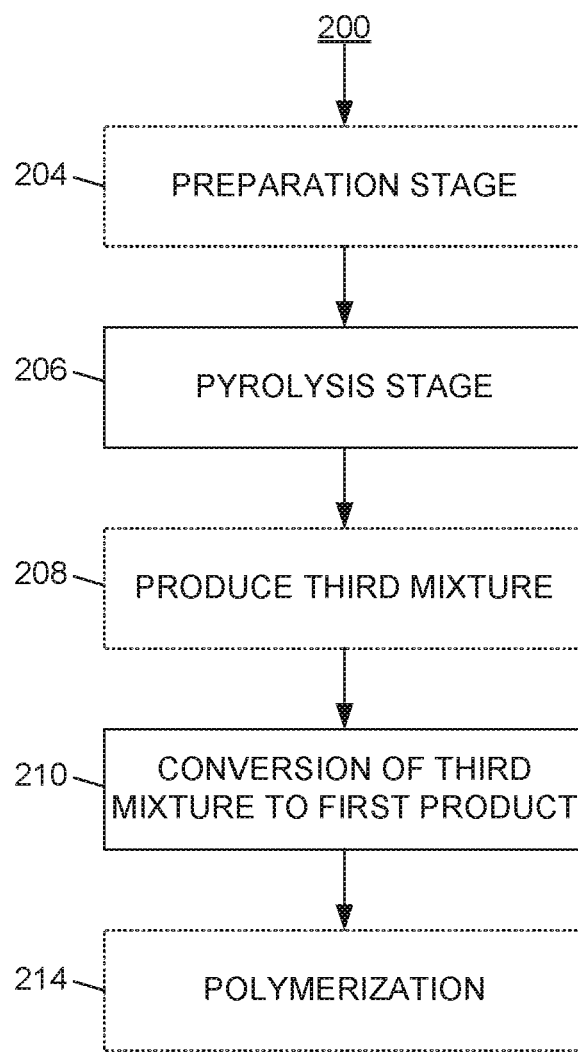
FIG. 1 schematically illustrates embodiments of the invention relating to converting hydrocarbon and oxygenate to a mixture comprising acetylene and carbon monoxide, converting at least a portion of the mixture's acetylene to ethylene, and then polymerizing at least a portion of the ethylene. Optional stages are enclosed by dashed lines.

One embodiment of the invention is based on the discovery of a process for converting a first mixture comprising hydrocarbon and oxygenate to a second mixture comprising $C_2$ unsaturates (ethylene and/or acetylene), hydrogen, and carbon monoxide; the relative amounts of the acetylene, hydrogen, and carbon monoxide being in ranges that are useful for selectively converting at least a portion of the acetylene to ethylene. The process involves exposing the first mixture to a temperature ≥1400° C. (which as used herein means $1.40 \times 10^{3}$° C. i.e., three significant digits), and results in (i) the conversion of a significant amount of the hydrocarbon in the first mixture to ethylene, acetylene, hydrogen, and carbon monoxide and (ii) utilizing at least a portion of the carbon monoxide and the hydrogen to selectively convert at least a portion of the acetylene to ethylene in the presence of an acetylene conversion catalyst. The invention is based in part on the following discoveries: (i) that exposing such a mixture to a temperature ≥$1.40 \times 10^{3}$° C. results in the conversion of at least a portion of the hydrocarbon and oxygenate in the mixture to carbon monoxide, instead of to higher molecular weight (and less useful) oxygen-containing compositions such as carbon dioxide and (ii) that the conversion produces a acetylene and carbon monoxide in relative amounts that are useful for selectively converting the acetylene to ethylene.

In an embodiment, a second mixture is derived from the first mixture by thermal pyrolysis of the first mixture, e.g., in a pyrolysis reactor. For example, it has been found that a high-temperature (e.g., ≥$1.40 \times 10^{3}$° C.) thermal pyrolysis reactor can be configured to convert a portion of the first mixture to a second mixture containing a significantly greater amount of acetylene than would be present under similar reaction conditions at a lower temperature. It has also been found that utilizing a high-temperature thermal pyrolysis reactor results in the conversion of methane, when that species is contained in the first mixture. For example, at a thermal pyrolysis temperature ≥$1.40 \times 10^{3}$° C. and pyrolysis reactor residence time <1.0 seconds, methane can be converted to $C_2$ unsaturates even at a total pressure≥atmospheric pressure. In embodiments where the second mixture's enthalpy is greater than that of the first mixture, the process of deriving the second mixture from the first mixture can involve abstracting heat from the first region (and components contained therein, e.g., articles, compositions, etc.). Optionally, at least a portion of the abstracted heat is produced by partially or completely oxidizing (e.g., combusting) at least a portion of a fourth mixture comprising oxidizable atoms and molecules (e.g., CO, hydrogen, hydrocarbon, etc.) in a fourth mixture, the oxidizing occurring in a second region that is at least partially coextensive with the first region. A fifth mixture, derived from the fourth mixture and comprising, e.g., products formed by oxidizing all or a portion of the fourth mixture, can be conducted away from the second region.

In one or more embodiments, byproducts are separated from one or more of the mixtures. For example, the process can further comprise at least one of: (i) separating from the fifth mixture a byproduct comprising oxygenate and utilizing least a portion of the separated byproduct to produce the first and/or fourth mixtures or (ii) separating from the second mixture a second byproduct comprising hydrocarbon and hydrogen and utilizing at least a portion of the separated second byproduct to produce at least one of the first, third, or fourth mixtures.

Pyrolysis is utilized in deriving the second mixture from the first mixture. Separation of undesired species and/or the addition of desired species can be utilized in deriving the third mixture from the second mixture. The process further comprises converting at least a portion of the second mixture's acetylene (e.g., as one component of a third mixture) to form a first product comprising ethylene. Optionally, the conversion is catalytic conversion that is conducted at least partially in the vapor or liquid phase and the catalyst comprises at least one element selected from Group VIII of the Periodic Table.

For the purpose of this description and appended claims, the following terms are defined. The term "hydrocarbon" means molecules (and mixtures thereof) including both carbon atoms and hydrogen atoms, and optionally including other atoms (heteroatoms) such as oxygen, sulfur, and nitrogen, wherein the carbon atoms and hydrogen atoms together comprise ≥75.0% of the atoms present in the molecule or mixture of molecules; but not including molecules comprising ≥5.0 atom % of oxygen atoms. For example, the term hydrocarbon does not include methanol. The term oxygenate means (i) oxygen atoms and (ii) molecules (and mixtures thereof) which include at least one oxygen atom wherein the oxygen atoms comprise ≥5.0 atom % based on the number of atoms present in the molecule or mixture of molecules, including those molecules which further comprise hydrogen, carbon, sulfur, and nitrogen.

The "Periodic Table of the Elements" means the Periodic Chart of the Elements as tabulated on the inside cover of The Merck Index, 12th Edition, Merck & Co., Inc., 1996.

The terms "convert", "conversion", "converting", etc. with respect to pyrolysis processes include, e.g., any molecular decomposition, cracking, breaking apart, reformation of molecules, including hydrocarbon, oxygenate, etc. by at least pyrolysis heat. With respect to non-pyrolysis processes that are at least partly catalytic, the term conversion includes, e.g. hydroprocessing (such as hydrogenation, hydrotreating, etc.), hydroformylation, catalytic separation, etc.

The terms "pyrolysis" and "pyrolysis chemistry" mean an endothermic reaction, e.g., the conversion of hydrocarbons to unsaturates such as ethylene and acetylene.

The term "reactor" means equipment and combinations thereof for chemical conversion, including reactor combinations and systems such as disclosed in U.S. Patent App. Pub. No. 2007/0191664. The term "pyrolysis reactor", as used herein, refers to a reactor, or combination or system thereof for converting hydrocarbons by at least pyrolysis. A pyrolysis reactor optionally includes one or more reactors and/or associated equipment and lines. The term pyrolysis reactor encompasses, e.g., the combination and system of first and second pyrolysis reactors described in U.S. Patent App. Pub. No. 2007/0191664. With respect to pyrolysis reactors, the term "residence time" means the average time duration for non-reacting (non-converting by pyrolysis) molecules (such as He, $N_2$, Ar) having a molecular weight in the range of 4 to 40 to traverse a pyrolysis region of a pyrolysis reactor. The terms "pyrolysis stage" means at least one pyrolysis reactor, and optionally means for conducting one or more feeds thereto and/or one or more products away therefrom. With respect to reactors, the term "region" means a location within a reactor, e.g., a specific volume within a reactor, a specific volume between two reactors and/or the combination of different disjointed volumes in one or more reactors. A "pyrolysis region" is a region for conducting pyrolysis. The term "thermal pyrolysis" means <50.0% of the heat utilized by the pyrolysis is provided by (a) exothermically reacting the pyrolysis feed, e.g., by exothermically reacting an oxidant with hydrocarbon and/or hydrogen of the first mixture and/or (b) contacting the pyrolysis feed with the products of combustion to heat the pyrolysis feed. The term "thermal pyrolysis reactor" means a pyrolysis reactor wherein ≥50.0% of the heat utilized by the pyrolysis is provided by heat transfer from reactor components, e.g., solid surfaces associated with the reactor such as tubulars or bed materials; optionally ≥80.0% or ≥90.0% of the heat utilized by the pyrolysis is provided by such heat transfer.

The term "high-severity operating conditions" means pyrolysis conditions resulting in the conversion of a mixture (e.g., the first mixture) comprising hydrocarbons to make a product having an acetylene content ≥10.0 wt. % based on the weight of the hydrocarbons in the pyrolysis feed. The operating conditions for a thermal pyrolysis reactor may be characterized by a severity threshold temperature that divides low-severity operating conditions in thermal pyrolysis reactors from high-severity operating conditions in thermal pyrolysis reactors. The severity threshold temperature is defined as the lowest temperature at which the feed to the reactor may react at a residence time ≤0.1 second to make at least 10.0 wt. % acetylene as a percent of the hydrocarbons in the mixture evaluated at the given operating conditions of the process. The high-severity operating conditions for a thermal pyrolysis reactor may be characterized as peak pyrolysis gas temperatures that are greater than the severity threshold temperature. The low-severity thermal pyrolysis reactor may be characterized as pyrolysis gas temperatures that are less than the severity threshold temperature and no pyrolysis gas temperatures that exceed the severity threshold temperature. For example, for the thermal conversion of a methane feed at a pressure of 14.7 psig (101 kPa) and with 2:1 molar ratio of molecular hydrogen to methane, the threshold temperature is about 1274° C. for this process. At temperatures at or above 1274° C., yields of acetylene can exceed 10.0 wt. % of feed hydrocarbon at some time ≤0.1 seconds. Conversely, at temperatures below 1274° C. there are no times ≤0.1 seconds for which yields of acetylene reach 10.0 wt. % of the methane.

The term "peak pyrolysis gas temperature" means the maximum temperature achieved by the bulk pyrolysis stream gases as they travel through the pyrolysis reactor (e.g., cracking region or radiant region). One skilled in the art will appreciate that temperatures immediately proximate to a partition may be higher, and may, in some infinitesimal boundary layer, actually approach the solid temperature. However, the pyrolysis temperature referred to herein should be considered a bulk gas temperature, which is a temperature that could be measured by a device (such as a thermocouple) that is not in contact with the solid material. For example, if the gas is traveling through tubulars in a thermal pyrolysis reactor, the bulk gas temperature may be taken as the average temperature over any tubular cross-section, and the peak pyrolysis gas temperature as the highest cross-sectional-average temperature of the pyrolysis stream.

In an embodiment, a second mixture is derived by pyrolysis of a first mixture, the first mixture being derived from one or more source materials. The term "source materials" means sources, containers, conduits, vessels, reservoirs, etc. of hydrocarbon and/or oxygenate. Examples of source materials comprising hydrocarbon include one or more of Fischer-Tropsch gases, syngas (a mixture comprising carbon monoxide and hydrogen), methane, methane containing streams such as coal bed methane, biogas, associated gas, natural gas and mixtures or components thereof, steam cracked gas oil and residues, gas oils, heating oil, jet fuel, diesel, kerosene, gasoline, coker naphtha, steam cracked naphtha, catalytically cracked naphtha, hydrocrackate, reformate, raffinate reformate, Fischer-Tropsch liquids, natural gasoline, distillate, virgin naphtha, crude oil, atmospheric pipestill bottoms, vacuum pipestill streams including bottoms, wide boiling range naphtha to gas oil condensates, heavy non-virgin hydrocarbon streams from refineries, vacuum gas oils, heavy gas oil, naphtha contaminated with crude, synthetic crudes, shale oils, coal liquefaction products, coal tars, tars, atmospheric resid, heavy residuum, C4's/residue admixture, naphtha residue admixture, cracked feedstock, coker distillate streams, or hydrocarbon streams derived from plant or animal matter. Example of source materials comprising oxygenate include one or more of oxygen ($O_2$), water (e.g., steam), carbon monoxide, carbon dioxide, alcohols (e.g., methanol, ethanol, etc.), ethers, acids (e.g., inorganic acids such as $H_2SO_4$ and organic acids such as hydrocarbon containing a carboxyl functionality), carbonyls, carbonates, carbamates, carbohydrates, non-volatile oxygenates, etc.

Optionally, one or more mixtures and/or source materials comprises hydrogen atoms. The term "hydrogen content" of a mixture or source material means atomic hydrogen bound to carbon and/or heteroatoms covalently bound thereto and which excludes molecular hydrogen ($H_2$) in the mixture (or source material) expressed as a weight percent based on the weight of the hydrocarbons in the mixture (or source material). Optionally, one or more mixtures and/or source materials comprises non-volatiles. The term "non-volatiles" means molecules and mixtures thereof having a nominal atmospheric boiling point ≥570.0° C., e.g., refractory oxygenates, refractory hydrocarbon, metals, minerals, etc. American Society of Testing and Materials ("ASTM") methods can be used to determine the nominal atmospheric boiling point (ASTM method 1078) and the amount and properties of such non-volatiles, such as ASTM methods D-6560, D-7061, D-189, D-482, D-524, and D-2415. Non-volatiles that are capable of being combusted are called "combustible non-volatiles". The term non-volatiles encompasses e.g., coke, ash, soot, resid, metal, mineral, ash, ash-forming asphaltenic, tar, etc., including those formed, e.g., during or after oxidation (e.g., combustion or partial oxidation) and/or pyrolysis, including those which may remain as a residue or deposit in the reaction region. Optionally, one or more mixtures and/or source materials comprises $C_{3+}$. The term "$C_{3+}$" means molecules having at least three carbon atoms, including, e.g., coke and soot, whether those products emerge from the reactor or remain within the pyrolysis reactor. The term "reactor effluent" means products of pyrolysis conducted away from the reactor. The reactor effluent comprises $C_2$ unsaturates, where the term "$C_2$ unsaturates" means hydrocarbon having two carbon atoms and ≤4 hydrogen atoms.

The term "combustion feed" means the two or more molecules or mixtures of molecules that are combined to form a combustion reaction, e.g., the fourth mixture. Any of the combustion feed, fuel, or oxidant may additionally include non-combustible but volatile diluent, such as $N_2$ and/or other inert gases.

Suitable reaction conditions; the first, second, third, fourth, and fifth mixtures; and related products and byproducts will now be described in more detail. Although the following features of the invention are described in terms of high-temperature thermal pyrolysis reactions, the invention is not limited thereto, and this description is not meant to foreclose other embodiments within the broader scope of the invention.

I. First Mixture

The first mixture generally comprises (i) hydrocarbon and (ii) oxygenate, and optionally further comprises (iii) hydrogen (as $H_2$) and (iv) diluent, the hydrocarbon and oxygenate being as defined in the preceding section. The type of hydrocarbon is not critical; e.g., the hydrocarbon can even compromise hydrocarbon non-volatiles, including those that are not in the gas phase at the temperature, pressure, and composition conditions subsisting at the inlet to the pyrolysis reactor. Optionally, (i) the first mixture further comprises molecular hydrogen, (ii) the hydrocarbon of the first mixture comprises methane, and (iii) the oxygenate of the first mixture comprises carbon monoxide.

The hydrocarbon and oxygenate of the first mixture can be derived from one or more source materials, as defined in the preceding section. Optionally, a hydrocarbon source material has, e.g., a hydrogen content in the range of 6.0 wt. % to 25.0 wt. %, 8.0 wt. % to 20.0 wt. % (e.g., not natural gas), or 20.0 wt. % to 25.0 wt. % (e.g., natural gas). In a particular embodiment, the hydrocarbon of the first mixture is derived from natural gas (e.g., a gas of synthetic and/or geological origin). The first mixture can comprise, e.g., upgraded natural gas (such as natural gas that has been sweetened and/or dehydrated). Besides methane, natural gas commonly includes other hydrocarbons (such as ethane and other alkanes), generally in amounts greater than or equal to the amount of methane in the natural gas on a weight basis. Optionally, the natural gas further comprises oxygenate (e.g., water. $CO_2$, etc.) and/or diluent (e.g., hydrogen sulfide, nitrogen, etc.), which can be used as a source of at least a portion of the oxygenate (in the case of water, $CO_2$) and/or diluent (in the case of nitrogen) in the first mixture. Optionally, the oxygenate of the first mixture is derived from the same source material as the hydrocarbon (e.g. both the hydrocarbon and oxygenate are derived from natural gas). Alternatively, the oxygenate is derived from at least a second source material, e.g., one comprising one or more of oxygen ($O_2$), water (e.g., steam), carbon monoxide, carbon dioxide, acid (e.g., inorganic acids such as $H_2SO_4$ and organic acids such as hydrocarbon containing a carboxyl functionality), carbonyls, carbonates, carbamates, carbohydrates, non-volatile oxygenates, etc.

In an embodiment where the first mixture's oxygenate comprises ≥90.0 wt. % carbon monoxide based on the weight of the first mixture's oxygenate, the first mixture can comprise ≥200.0 ppmm (parts per million on a molar basis) of oxygenate, e.g., an oxygenate amount in the range of $2.0 \times 10^2$ ppmm to $3.0 \times 10^4$ ppmm, such as $5.0 \times 10^2$ ppmm to $2.0 \times 10^4$ ppmm per mole of the first mixture. In an embodiment, the first mixture has an O:C atomic ratio in the range of $4.0 \times 10^{-4}$ to $1.0 \times 10^{-1}$, such as 0.0020 to 0.050. The O:C atomic ratio is defined as the ratio of oxygen atoms (as the total number of oxygen atoms in the first mixture) to carbon atoms (as all carbon atoms in the first mixture that are not bound to oxygen atoms, e.g., as can be determined by Nuclear Magnetic Resonance Spectroscopy). For example, the denominator of this ratio can be equal to the number of carbon atoms bound to the first mixture's hydrocarbon. Optionally, the first mixture comprises ≥0.01 mole of hydrocarbon, e.g., 0.1 mole % to 90 mole % of hydrocarbon; and ≥0.01 mole % of molecular hydrogen, e.g., 0.1 mole % to 90 mole % of molecular hydrogen, the mole percents being based on the sum of the number of moles of hydrocarbon, oxygenate, and molecular hydrogen in one mole of the first mixture. When an oxygenate other than carbon monoxide is utilized, the amount of oxygenate (as defined by the O:C ratio) is equal to (a) the amount of oxygenate that would have been used if the oxygenate were carbon monoxide divided by (b) the Effectiveness Factor corresponding to the oxygenate that is actually used. For example, the first mixture O:C ratio is set equal to (a) the O:C ratio that would have been used if the oxygenate were carbon monoxide divided by (b) the Effectiveness Factor corresponding to the oxygenate that is actually used. The Effectiveness Factor can be readily determined by one skilled in the art of pyrolysis as the fraction of first mixture oxygenate oxygen atoms that emerge from pyrolysis as carbon monoxide molecules in the second mixture. The Effectiveness Factors for selected oxygenates is set out in the following table, those Effectiveness Factors being based on exposing a feed comprising methane, molecular hydrogen, and oxygenate under a wide range of conditions effective to result in a 50 to 70% conversion of the methane, including peak pyrolysis temperatures ranging from 1400° C. to 1800° C., pressures from 1.3 to 2.0 bar (absolute), and residence times from about 1 to 50 millisecond. It has been found that the Effectiveness Factor is approximately constant over this broad range, as long as conditions are effective to result in about 50 to 70% hydrocarbon conversion. When the oxygenate is a mixture of two or more oxygenates, the mixture's Effectiveness Factor is approximately equal to the linear combination of the individual oxygenate's Effectiveness Factors. For example, when the oxygenate is a mixture of X mole % of carbon monoxide, Y mole % of water, and Z mole % of carbon dioxide, the mixture's Effectiveness Factor=X·1.0+Y·0.05+Z·0.55. In an embodiment, the Effectiveness Factor is ≥0.1, e.g., ≥0.2, such as ≥0.4. Optionally, the oxygenate comprises ≥75.0 wt. % of carbon monoxide and/or carbon dioxide based on the weight of the oxygenate, e.g., ≥90.0 wt. %, such as ≥99.0 wt. %. Optionally, the oxygenate is carbon monoxide. Optionally, the first mixture comprises natural gas, the natural gas comprising ≥10.0 wt. % of methane, e.g., ≥25.0 wt. %, and ≥1.0 wt. % of carbon dioxide, e.g., ≥10.0 wt. %; the weight percents being based on the weight of the natural gas.

TABLE

| Oxygenate | Effectiveness Factor |
|---|---|
| Carbon Monoxide | 1.0 |
| Water | 0.05 |
| Molecular Oxygen ($O_2$) | 0.15 |
| Carbon Dioxide | 0.55 |
| Methanol | 0.95 |
| Ethanol | 0.65 |

When the first mixture comprises molecular hydrogen, the first mixture optionally has a molecular hydrogen to carbon (as all carbon atoms in the first mixture that are not bound to oxygen atoms, e.g., as can be determined by Nuclear Magnetic Resonance Spectroscopy) molar ratio in the range of from 0.0 to 5.0, e.g., 0.1 to 4.0, such as 1.0 to 3.0 or 1.0 to 2.0. Optionally, the first mixture has a hydrogen (all hydrogen atoms in the first mixture regardless of atomic or molecular form) to carbon (all carbon atoms in the first mixture regardless of atomic or molecular form) atomic ratio in the range of from 1.0 to 15.0. e.g., in the range of from 4.0 to 8.0.

Optionally, the first mixture further comprises diluent, e.g., ≥1.0 wt. % of diluent based on the weight of the first mixture. Suitable diluents (which can be a diluent mixture) include one or more of nitrogen ($N_2$), hydrogen sulfide, $C_{4+}$ mercaptans, amines, mixtures of amines, non-hydrocarbon non-volatiles (whether combustible or not) including refractory inorganics such as refractory oxygenates, inert gas (including inert gas mixtures), etc. In an embodiment, the first mixture comprises ≤10.0 wt. % diluent.

The first mixture optionally comprises a total amount of non-combustible non-volatiles (e.g., ash; ASTM D-189), from all sources, ≤2.0 parts per million weight (ppmw) based on the weight of the first mixture, e.g., ≤1.0 ppmw. Optionally, the first mixture comprises a total amount of combustible non-volatiles (e.g., tar, asphaltenes. ASTM D-6560) in the first mixture, from all sources, ≤5 wt. % based on the weight of the hydrocarbon in the first mixture, e.g. ≤1.0 wt. %, such as ≤100.0 ppmw or ≤10.0 ppmw, provided the presence of the combustible non-volatiles does not result in ≥2.0 ppmw (e.g. ≥1.0 ppmw) based on the weight of the second mixture.

In one or more embodiments, the first mixture optionally has one or more of the following properties: at least 15.0 wt. % of the molecular hydrogen in the first mixture (based on the total weight of the molecular hydrogen in the first mixture) is molecular hydrogen derived from the second mixture or one or more products thereof. In another embodiment, the first mixture comprises ≥50.0 ppm sulfur based on the weight of the first mixture.

II. Process for Deriving the Second Mixture

The second mixture is derived from the first mixture by exposing the first mixture to a temperature ≥1.40×10³° C. under pyrolysis conditions. The process is illustrated schematically in FIG. 1. The first mixture is derived from one or more source materials (200), the source materials optionally being upgraded in optional preparation stage (204). Optional preparation stage (204) can be utilized for one or more of (i) separating one or more of hydrocarbon, non-combustible nonvolatiles, oxygenate, molecular hydrogen, or diluent from the source material, (ii) adding one or more of hydrocarbon, oxygenate, molecular hydrogen, or diluent to the source material, (iii) thermally upgrading (e.g., coking or visbreaking) the source material, or (iv) catalytically upgrading (e.g., hydroprocessing, such as hydrotreating) the source material, etc. When utilized in connection with one or more of (ii)-(iv), added hydrocarbon, oxygenate, molecular hydrogen, or diluent can be obtained, e.g., from sources external to the process, from byproducts separated from the second or fifth mixtures, etc.

Accordingly, the process is compatible with a first mixture that includes a broader range of hydrocarbon (e.g., methane, hydrocarbon with significantly lower hydrogen intrinsic content than methane, high molecular weight hydrocarbon, aromatic hydrocarbon, etc.) which have not been observed to form an appreciable amount of the specified second mixture when exposed to a temperature <1.40×10³° C. In other words, the process is advantageous in that it may utilize a first mixture comprising a broad range of hydrocarbon in pyrolysis stage 206, even without upgrading in preparation stage (204) to form the specified second mixture.

In an embodiment, a first mixture comprising (a) oxygenate and (b) hydrocarbon is conducted to pyrolysis stage 206. It has been discovered that exposing such a first mixture to a temperature ≥1.40×10³° C. under pyrolysis conversion conditions results in ≤20.0 wt. % combustible non-volatile hydrocarbon (e.g., coke) in the second mixture, generally at least part of which is deposited as a residue in the pyrolysis stage. Optionally, at least one of the pyrolysis reactors of stage 206 is a thermal pyrolysis reactor, e.g., a regenerative thermal pyrolysis reactor. In the case of a regenerative reactor, at least a portion of the non-volatile hydrocarbon can be oxidized and conducted away from the pyrolysis stage during regeneration, as discussed in the following sections. At least a portion of the heat derived from this oxidation can be used in, e.g., the pyrolysis reaction for deriving the second mixture from the first mixture.

Preparation stage 204 is optional. In other words, the first mixture can comprise (or consist essentially of, or even consist of) hydrocarbon and oxygenate obtained directly from source materials (200) such as natural gas and air, optionally with no intervening process steps. Following the optional preparation stage 204, the first mixture is conducted to the pyrolysis stage (206) wherein it is exposed to a temperature ≥1.40×10³° C. under pyrolysis conditions, e.g., thermal pyrolysis conditions, to convert at least a portion of the first mixture to the second mixture. At least a portion of the second mixture, e.g., a portion which comprises $C_2$ unsaturates, hydrogen, and carbon monoxide, is conducted away from the pyrolysis stage to an optional upgrading stage (208) for, e.g., separation of a first separated portion. The first separated portion can comprise, e.g., of one or more of hydrocarbons (such as saturated hydrocarbon and/or those containing one or more heteroatoms), diluent, non-volatiles, saturated hydrocarbons, and hydrogen, etc. Optionally, a second portion is separated from the second mixture, the second portion comprising, e.g., a portion of the second mixture that is not in the vapor phase at the downstream end of the pyrolysis reactor of stage 206. Optionally, the second portion remains in the pyrolysis stage (e.g., in the pyrolysis reactor), e.g., as coke. In this embodiment, the third mixture, thus derived from the second mixture by the separations occurring in stages 206 and/or 208, is conducted away from stage 208. In embodiments where, e.g., (i) no portion of the second mixture remains in stage 206 and/or (ii) optional stage 208 is not used, the third mixture comprises, consists essentially of, or even consist of the second mixture. In another embodiment, the third mixture comprises, consists essentially of, or even consist of that portion of the second mixture which is in the vapor phase at the downstream end of the pyrolysis of stage 206. In yet another embodiment, the third mixture is derived from the second mixture by exposing at least a portion of the second mixture to a temperature <100.0° C. and separating from the second mixture one or more of coke, heteroatom species, or saturated hydrocarbons.

The third mixture is conducted to stage 210 for conversion of at least a portion of the third mixture's acetylene to a first product comprising ≥90.0 mole % ethylene per mole of $C_2$ unsaturates in the product, e.g., ≥95.0 mole %, such as ≥99.9 mole %. In an embodiment, the first product is conducted away from stage 210 to stage 214, where at least a portion of the ethylene in the product is polymerized, e.g., to form a second product comprising polymer such as polyethylene homopolymer or copolymer. Conventional acetylene conversion and olefin polymerization processes are suitable for stages 210 and 214, but the invention is not limited thereto. In an embodiment, the process further comprises dividing at least a portion of the first product in a stage 212 into first and second portions, wherein the first portion is conducted to stage 214 and the second portion is utilized for deriving the third mixture from the second mixture, e.g., by combining with the second portion of the first product at least a portion of the second mixture, such as with a portion of the second mixture conducted away from stage 206 or with a portion of the upgraded second mixture conducted away from stage 208.

Figure 2A:
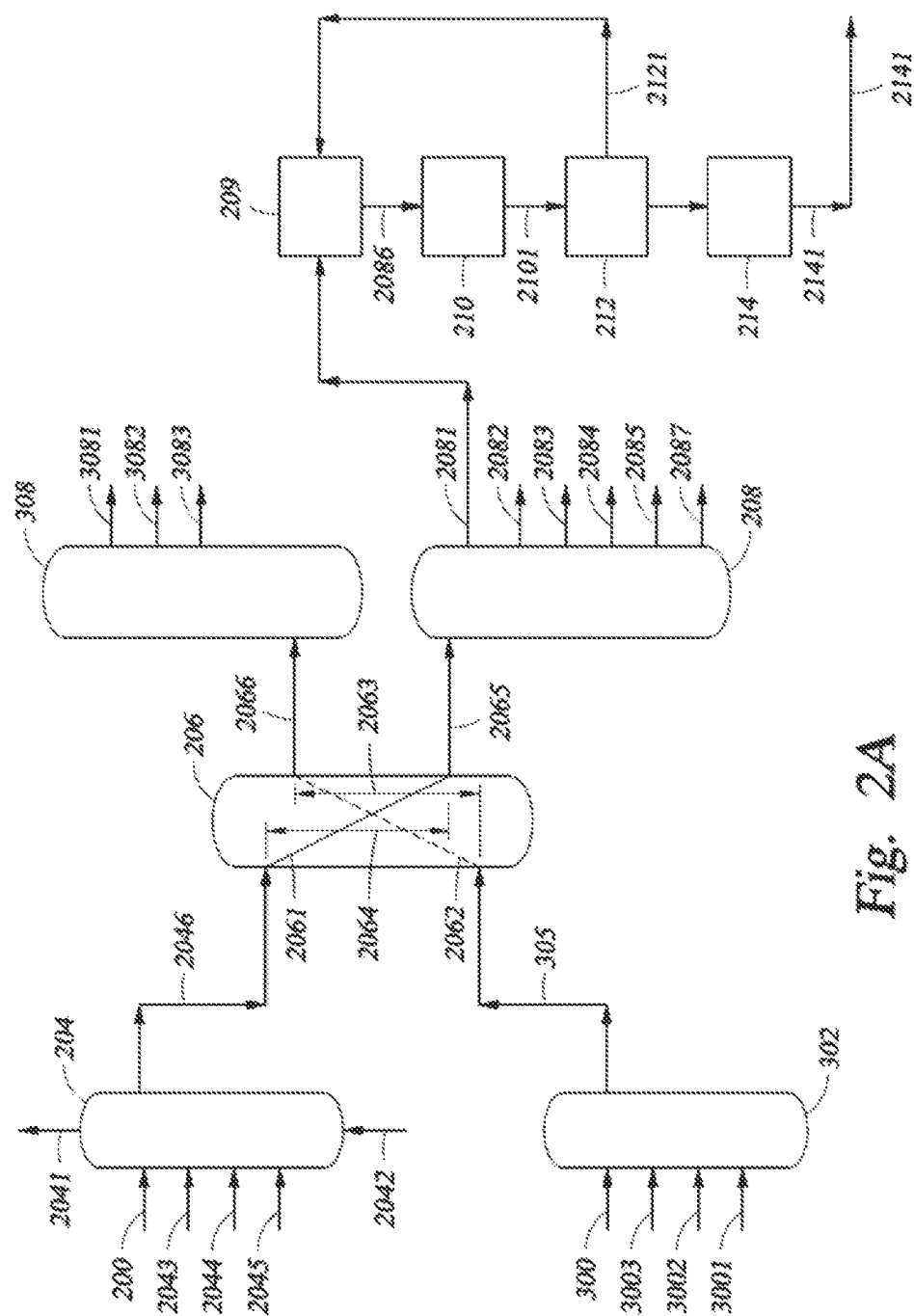
FIGS. 2A and 2B schematically illustrate an embodiment of the invention utilizing a reverse-flow pyrolysis reactor.

Although process (e.g., as illustrated in FIG. 2) is compatible with "back end" acetylene conversion, e.g., the acetylene converting occurs downstream of optional stage 208, the invention is not limited thereto. This description is not meant to foreclose other embodiments, such as those utilizing "front end" acetylene conversion, e.g. where acetylene conversion is conducted upstream of optional stage 208, those utilizing both front end and back end acetylene converters, and those that do not include optional stage 208.

The pyrolysis stage 206 will now be described in more detail. While not wishing to be bound by any theory or model, it is believed that exposing the first mixture to a temperature ≥1.40×10³° C. results in conversion of at least a portion of the first mixture to a second mixture, the second mixture having a carbon monoxide to acetylene molar ratio in the range of 2.5×10⁻³ to 1.0 and comprising ≥1.0 wt. % $C_2$ unsaturates based on the weight of the second mixture. It has been discovered that converting the first mixture at a temperature ≥1.40×10³° C. by pyrolysis results in a second mixture that (i) contains carbon monoxide in an amount useful for catalytically converting acetylene to ethylene with increased selectivity (less ethylene saturation) and (ii) has a molar ratio of oxygenate molecules having ≥2 oxygen atoms:acetylene ≤0.1, e.g., ≤0.01, such as ≤0.001.

Conventional pyrolysis reactors are suitable for use in stage 206, but the invention is not limited thereto. Suitable reactors include, for example, regenerative reverse flow reactors as described in U.S. Patent App. Pub. No. 2007/0191664 and thermal pyrolysis reactors as described in U.S. Pat. No. 7,491,250; U.S. Patent Application Ser. No. 61/349,464; and U.S. Patent App. Pub. Nos. 2007/0144940; and 2008/0142409, all of which are incorporated by reference herein in their entirety. Optionally, the thermal pyrolysis is conducted under high-severity thermal pyrolysis conditions, e.g. by exposing the first mixture to temperature in the range of about 1.40×10³° C. to about 2.30×10³° C., e.g., in the range of about 1.45×10³° C. to about 1.80×10³° C. In an embodiment where the reactor's temperature is relatively constant over the reaction region, as may be the case when the pyrolysis reactor is a tubular reactor heated by a burner located in proximity to the outside of the tube, the first mixture achieves a peak pyrolysis gas temperature in the range of about 1.50×10³° C. to about 1.675×10³° C., e.g., in the range of about 1.54×10³° C. to about 1.65×10³° C. In embodiments where the reactor's temperature exhibits significant variation over the reaction region, as may be the case in a regenerative, reverse-flow pyrolysis reactor, the first mixture achieves a peak pyrolysis gas temperature in the range of about 1.40×10³° C. to about 2.20×10³° C., e.g., in the range of about 1.45×10³° C. to about 1.80×10³° C.

Optionally, ≥25.0 wt. % (such as of the ≥50.0 wt. % or ≥75.0 wt. %) of the first mixture achieves a peak pyrolysis gas temperature ≥1.40×10³° C., e.g., in the range of about 1.50×10³° C. to about 1.675×10³° C. based on the weight of the first mixture.

The peak pyrolysis gas temperature can be regulated to produce the desired amount of carbon monoxide in the second mixture, e.g., into a range that optimizes the selectivity of the acetylene conversion catalyst utilized in stage 210, i.e., increases the rate of acetylene conversion to ethylene and/or decreasing the rate of ethylene conversion to ethane and other saturated molecules. For example, it is observed that exposing the first mixture to a peak pyrolysis gas temperature ≥1.54×10³° C. increases the relative amount of carbon monoxide in the second mixture and decreases the amount of that portion of the non-volatiles in the second mixture as are produced by the pyrolysis. Optionally, stage 206 operates at a total pressure ≥10.0 mbar (absolute), e.g., in the range of 0.10 bar to 20.0 bar, such as 1.0 bar to 20.0 bar, or 2.0 bar to 7.0 bar.

The pyrolysis can be conducted for a time duration ($t_1$) sufficient for exposing ≥50.0 wt. %, e.g., ≥75.0 wt. %, such as ≥90.0 wt. % of the first mixture (based on the weight of the first mixture) to pyrolysis conditions for a residence time ≤about 0.3 seconds, e.g., ≤0.05 seconds. In an embodiment, $t_1$ is ≤10.0 seconds, e.g., ≤5.0 seconds, such as ≤1.0 seconds. Optionally, $t_1$ is in the range of 1.0×10⁻³ seconds to 10.0 seconds.

In an embodiment, the pyrolysis is high-severity thermal pyrolysis and includes one or more of the following conditions: the first mixture achieves a peak pyrolysis gas temperature ≥1.40×10³° C., e.g., in the range of 1.45×10° C. to 2.20×10³° C., such as, 1.50×10³° C. to 1.90×10³° C., or 1.60×10³° C. to 1.70×10³° C.; a total pressure ≥1.0 bar (absolute). e.g., in the range of 1.0 bar to about 15 bar, such as in the range of 2.0 bar to 10.0 bar; a residence time (during high severity conditions) ≤0.1 seconds, e.g., ≤5.0× 10⁻² seconds, such as ≤5.0×10⁻³ seconds and/or a $t_1$ in the range of 1.0×10⁻³ seconds to 10.0 seconds.

Although the process is robust and can operate within a wide range of pyrolysis conditions, e.g., temperature, pressure, residence times, severity, etc., the conditions are to generally selected to increase the relative amount of $C_2$ unsaturates in the second mixture, e.g., to increase the acetylene to $C_{3+}$ weight ratio. Relatively long residence times can result in over-cracking of the feed molecules, leading to an undesirable increase in the amount of methane and/or $C_{3+}$ in the second mixture. In an embodiment, residence time is ≤about 0.3 seconds, e.g., ≤0.05 seconds. In an embodiment, the pyrolysis is high-severity, thermal pyrolysis and the residence time is ≤0.05 seconds, such as ≤0.02 seconds. Residence time can be selected, e.g., for optimum $C_2$ unsaturates' yield under pyrolysis conditions. This can be done by measuring the amount of $C_2$ unsaturates in the second mixture under substantially constant thermal pyrolysis conditions at a plurality of residence times. The optimum residence time can be approximated using conventional interpolation and extrapolation of the measured values. The optimum residence time can also be approximated using pyrolysis reaction simulations of second mixture composition as a function of pyrolysis conditions and residence time, including conventional pyrolysis reaction simulations.

In one or more embodiments, at least a portion of second mixture, e.g., a portion of the second mixture that is in the vapor phase at the downstream end of stage 206, is conducted to a conversion stage (210) for catalytically converting at least a portion of the third mixture's acetylene to a first product. In related embodiments, a third mixture is conducted to stage 210, the third mixture being derived from at least a portion of the second mixture, e.g., the portion that is in the vapor phase at the downstream end of stage 206. The third mixture has a carbon monoxide to acetylene molar ratio in the range of $5.0 \times 10^{-4}$ to 1.5 and comprises $A_1$ wt. % of saturated hydrocarbon, $A_2$ wt. % of acetylene, and $A_3$ wt. % of ethylene based on the weight of the third mixture; the first product comprises $A_4$ wt. % of saturated hydrocarbon, $A_5$ wt. % of acetylene, and $A_6$ wt. % of ethylene based on the weight of the first product; and wherein $A_6 \geq A_3$, $A_5 < A_2$, and $(A_6-A_3)/(A_2-A_5) \geq 0.50$, e.g., $\geq 0.70$, such as $\geq 0.80$. Optionally, $A_1 \geq 1.0$ and $A_4 \geq 1.0$. The third mixture can be derived from the second mixture by way of an optional upgrading stage (208), which will now be described in more detail. Optionally, the acetylene conversion is catalytic conversion which is conducted at least partially in the vapor or liquid phase and wherein (a) the catalyst comprises at least one element selected from Groups Ia, Ib, IIb, and/or VIII of the Periodic Table and (b) $(A_6-A_3)/(A_2-A_5) \geq 0.70$.

Stage 208 can include upgrading means, e.g., means for removing from the second mixture one or more of hydrocarbon (such as saturated hydrocarbon and/or those containing one or more heteroatoms), diluent, non-volatiles, and hydrogen, etc. For example, stage 208 can include one or more of a tar and/or solid removal means, compression means, adsorption means, distillation means, washing means, or drying means. While stage 208 can encompass conventional processing, e.g. conventional separation means, the invention is not limited thereto. Separation means can be used, e.g., for removing condensable species (e.g., condensable hydrocarbon) from the second mixture. Such condensable species may include vaporized liquids that condense, such as benzene, or those that can be separated via, e.g., cooled separations for example, adsorption, vapor liquid separators, flash drums etc. Suitable separations means include conventional distillation or refrigerated distillation means such as one or more of demethanators and $C_2$ splitters, etc., but the invention is not limited thereto. The invention is compatible with low-pressure demethanizers and high-pressure demethanizers (e.g., those operating at a pressure $\geq 3.5$ MPa). Stage 208 can include contacting the second mixture or a portion thereof with a fluid having a pH $>7.0$.

Stage 208 can be utilized for removing at least a portion of any light-gas in the second mixture (e.g., one or more of hydrogen, light saturated hydrocarbon such as methane, carbon dioxide, hydrogen sulfide, etc.). Suitable light-gas removal means include one or more of separation, basic wash (e.g., caustic wash or amine scrubbing), etc. Optionally, the separation means includes one or more of pressure swing adsorption, membranes and/or cryogenic distillation, electrochemical separation, or liquid absorption. Light-gas separation means may be used to separate hydrogen, carbon monoxide, methane, nitrogen or other light gases. Optionally, the removed light gas can be used, e.g., to adjust the stoichiometry of the first or fourth mixtures (e.g., by increasing the hydrogen and/or diluent content, etc.), as a stripping medium (e.g., for upgrading one or more sources from which the first mixture is derived, such as by stripping upstream of stage 206, e.g., in stage 204), etc. For example, should the second mixture contain more hydrogen than is needed for acetylene conversion, at least a portion of the hydrogen in the second mixture can be removed, e.g., by partially cooling the second mixture (optionally at essentially constant pressure) to condense at least a portion of the second mixture and then separating therefrom a vapor comprising hydrogen. The separated hydrogen can be conducted away, e.g., for recycle to produce the first or fourth mixtures.

Optionally, stage 208 includes means for removing at least a portion of any water present in the second mixture, e.g., by one or more of a methanol treatment, such as those described in Belgian Patent No. 722,895, adsorption, extraction by diethylene glycol, etc. For example, stage 208 can include one or more driers located, e.g., downstream of caustic treatment, for removing at least a portion of the water, including conventional driers, e.g., molecular sieve dryers.

When the acetylene conversion of stage 210 occurs downstream of stage upgrading/separation stage 208 (e.g., when back-end acetylene conversion is utilized as illustrated in FIG. 2), stage 208 can include, e.g., means for cooling and then compressing the second mixture conducted away from stage 206 in order to produce the third mixture. For example, in embodiments where stage 206 has an outlet pressure that is less than the inlet pressure of the converter of stage 210, stage 208 can include, e.g., compressing at least the portion of the second mixture from which the third mixture is derived in order to achieve the desired stage 210 inlet pressure. Should the second mixture comprise acid gases (e.g., $CO_2$ and/or $H_2S$), these can be removed, e.g., downstream of the compression—a desirable location since the gas volume has been reduced significantly during compression. Conventional methods are suitable for removing acid gases, e.g., caustic treatment, but the invention is not limited thereto. Acid gases separated from the second mixture can be conducted away, e.g., for storage or further processing such as in a Claus plant.

Stage 208 can be utilized to produce the third mixture by combining at least a portion of the second mixture with added species, such as molecules obtained from other stages of the process. For example, at least a portion of the product of the acetylene conversion of stage 210 (whether front end or back end) can be separated and conducted upstream of stage 210 (and/or upstream of one or more conversion zones thereof when more than one conversion zone is utilized), e.g., to stage 208 to increase the amount of ethylene in the third mixture. In other words, in one embodiment the third mixture comprises a portion of the second mixture to be conducted to the acetylene converter 210 and further comprises one or more of ethylene, methane, or hydrogen recycled from downstream of the acetylene converter.

Optionally, at least a portion of the hydrogen, saturated hydrocarbon, diluent, etc., separated from C2 unsaturates in upgrading stage 208 are recycled, e.g., by combining such separated species with one or more of the first mixture's source materials, e.g., in preparation stage 204. The second mixture and third mixtures will now be described in more detail.

III. The Second and Third Mixtures

When the first mixture, as defined in Section I, is subjected to the pyrolysis conditions defined in Section II, the second mixture has a carbon monoxide to acetylene molar ratio in the range of $2.5\times10^{-3}$ to 1.0 and comprises an amount ($A_7$) of $C_2$ unsaturates ≥1.0 wt. % based on the weight of the second mixture. For example, the second mixture can comprise $2.0\times10^2$ ppmm to $2.5\times10^4$ ppmm of carbon monoxide, e.g., $5.0\times10^2$ ppmm to $1.0\times10^4$ ppmm of carbon monoxide per mole of the second mixture. Optionally, the second mixture further comprises an amount ($A_8$) of $C_{3+}$ hydrocarbon, including $C_{3+}$ hydrocarbon which might remain within the pyrolysis region. Ag can be, e.g., ≥1.0 wt. % based on the weight of the second mixture, e.g., in the range of 1.0 wt. % to 20.0 wt. %. Optionally, the second mixture has a ratio of $A_8$ to $A_7$ of ≤about 0.5, e.g., ≤about 0.4, such as ≤about 0.3. Optionally, the second mixture has one or more of the following additional properties: an acetylene:ethylene molar ratio in the range of about 0.5 to about 20.0, e.g., about 1.20 to about 10.0, such as about 2.0 to about 10.0; a molecular hydrogen:$C_2$ unsaturates molar ratio in the range of 2.0 to 15.0; a molecular hydrogen:acetylene molar ratio ≥3.0, e.g., in the range of 3.0 to 30.0; a molecular hydrogen:ethylene molar ratio ≥1.0, e.g., in the range of 1.0 to 100.0; a carbon monoxide: acetylene molar ratio in the range of $3.5\times10^{-3}$ to 0.20, such as 0.005 to 0.050; or a carbon dioxide:$C_2$ unsaturates molar ratio ≤0.30. In an embodiment, the second mixture has a carbon monoxide: acetylene molar ratio in the range of 0.0035 to 0.20 and comprises $2.0\times10^2$ ppmm to $1.0\times10^4$ ppmm of carbon monoxide per mole of the second mixture. In embodiments, e.g., where the second mixture is derived from the first mixture under substantially isothermal conditions, the second mixture can have an acetylene:ethylene molar ratio ≥about 5.0, e.g., ≥about 10.0, such as ≥about 20.0. Optionally, (i) the second mixture comprises $5.0\times10^2$ ppmm to $1.0\times10^4$ ppmm of carbon monoxide per mole of the second mixture and/or (ii) the second mixture has a carbon monoxide to acetylene molar ratio in the range of $2.5\times10^{-3}$ to 1.0.

When the second mixture is upgraded in stage 208 as described in Section II, the third mixture has a carbon monoxide to acetylene molar ratio in the range of 0.01 to 1.5 and comprises $A_1$ wt. % of saturated hydrocarbon, $A_2$ wt. % of acetylene, and $A_3$ wt. % of ethylene based on the weight of the third mixture. The third mixture can comprise, e.g., $1.0\times10^3$ ppmm to $2.5\times10^4$ ppmm of carbon monoxide. Optionally, the third mixture has a carbon monoxide:acetylene molar ratio in the range of 0.04 to 0.50 and a molecular hydrogen:acetylene molar ratio in the range of 1.0 to 50.0, the third mixture comprising (a) ≥2.0 wt. % $C_2$ unsaturates based on the weight of the third mixture and (b) $1.0\times10^3$ ppmm to $2.5\times10^4$ ppmm of carbon monoxide per mole of the third mixture.

Optionally, the third mixture comprises ≥0.5 wt. % of molecular hydrogen, e.g., ≥1.0 wt. %, such as in the range of about 1.0 wt. % to about 30.0 wt. % based on the weight of the third mixture. Optionally, $A_1$ is ≥0.0 wt. %, e.g., in the range of from about 0.0 wt. % to about 60.0 wt. %, such as 5.0 wt. % to 50.0 wt. % based on the weight of the third mixture; $A_2$ is ≥0.5 wt. %. e.g., in the range of from about 0.5 wt. % to about 15.0 wt. %, such as 1.0 wt. % to 10.0 wt. % based on the weight of the third mixture; and $A_3$ is ≥10.0 wt. %, e.g., in the range of from about 15.0 wt. % to about 99.0 wt. %, e.g., 30.0 wt. % to 90.0 wt. % based on the weight of the third mixture. The balance of the third mixture (to equal 100.0 wt. %) can comprise, e.g., diluent Optionally, the third mixture is substantially free of $C_{3+}$, e.g., $C_{3+}$ hydrocarbon. For example, the third mixture can comprise $C_{3+}$ hydrocarbon in an amount ≤1.0 wt. %. e.g., ≥0.01 wt. % based on the weight of the third mixture. Optionally, the third mixture has one or more of the following additional properties: an acetylene:ethylene molar ≤1.0. ing molar ratio, e.g., in the range of about 0.01 to about 1.0, such as in the range of about 0.05 to about 0.50; a molecular hydrogen:$C_2$ unsaturates molar ratio ≥0.1. e.g., in the range of 0.1 to 20.0; a molecular hydrogen:acetylene molar ratio ≥1.0, e.g., in the range of 1.0 to 40.0; a molecular hydrogen:ethylene molar ratio ≥0.1, e.g., in the range of 0.1 to 50.0; or a molar ratio of molecular hydrogen to carbon monoxide ≥1.0, e.g., in the range of from about 1.0 to about 1000.0, such as in the range of from about 2.0 to about 200.0, or in the range of from about 2.0 to about 100.0.

The first product can be derived from the third mixture in stage 210, e.g., by catalytically converting at least a portion of the third mixture's acetylene to ethylene. An example of one such conversion process, utilizing front-end and/or back-end acetylene converters operated at least partially in the vapor phase, will now be described in more detail. The invention is not limited to this conversion process, and the following description is not meant to foreclose other conversion processes within the broader scope of the invention, e.g., acetylene conversion operated in the liquid phase.

IV. Process for Deriving the First Product

In one or more embodiments, the third mixture is conducted to conversion stage 210, either directly (e.g., with no intervening steps) or after first being subjected to one or more separation/upgrading operations, e.g., in optional stage 208. In stage 210, at least a portion of the third mixture's acetylene is converted to ethylene. For example, stage 210 can include hydroprocessing wherein at least a portion of the molecular hydrogen, carbon monoxide, and $C_2$ unsaturates (particularly acetylene) in the third mixture are converted to a first product having an amount of ethylene (weight basis) that is greater than the amount of ethylene in the third mixture (weight basis). Preferably, the acetylene conversion is selective, e.g., the ratio $(A_6-A_3)/(A_2-A_5)\geq0.50$, such as ≥0.70. Optionally, the selective acetylene conversion is conducted using a selectivated acetylene conversion catalyst. For the purpose of this description and appended claims, a selectivated acetylene-conversion catalyst is a catalyst that (i) when operating under substantially constant catalytic acetylene conversion conditions utilizing a feed that comprises ≤100 ppmm carbon monoxide per mole of the feed is (ii) first exposed to an amount of carbon monoxide in the range of $1.0\times10^3$ ppmm to $2.5\times10^4$ ppmm per mole of feed, (iii) exhibits an increase in the ratio $(A_6-A_3)/(A_2-A_5)$ of at least 1.0%, e.g., at least 5.0%, wherein $A_6\geq A_3$ and $A_2>A_5$. In other words, a selectivated acetylene conversion catalyst is one having an increased selectivity for the conversion of acetylene to ethylene in the presence of a selectivating composition, where the selectivating composition comprises acetylene and $1.0\times10^3$ ppmm to $2.5\times10^4$ ppmm carbon monoxide per mole of the selectivating composition. Optionally, the selectivating composition comprises the second and/or third mixture, the catalyst being selectivated by at least a portion of the second mixture's (or third mixture's) carbon monoxide.

At least a portion of the third mixture's acetylene is converted therein to ethylene in the presence of a catalytically effective amount of an acetylene conversion catalyst. Conventional acetylene converter technology can be used, including conventional acetylene conversion catalysts. For example, stage 210 can include (i) one or more adiabatic acetylene converters and/or (ii) one or more isothermal acetylene converters, with stage 210 being located upstream of upgrading stage 208 (front-end acetylene conversion) and/or downstream of stage 208 (back-end acetylene conversion). Optionally, stage 208 is utilized for adding molecular hydrogen to the second mixture to increase the amount of molecular hydrogen in the third mixture. A stage 212 can be utilized for dividing a portion of the first product (e.g., by splitting) for recycle to the second mixture via a combiner stage (209). For example, ≥10.0 wt. %, such as ≥50.0 wt. %, or 90.0 wt. % of the first product can be split and conducted to stage 209 in order to increase the relative amounts of, e.g., ethylene, hydrogen, and/or saturated hydrocarbon in the third mixture. Stages 209 and 212 can also be utilized to recycle a significant amount of carbon monoxide in the first product to the third mixture, e.g., ≥10.0 wt. % of the first product's carbon monoxide based on the weight of the first product, since little if any carbon monoxide is consumed in the acetylene conversion of stage 210. Such recycle optionally lessens the amount of oxygenate needed in the first mixture (which lessens the amount of carbon monoxide in the second mixture) while maintaining the desired carbon oxide:acetylene ratio in the third mixture, resulting in a more efficient process.

Examples of catalytic acetylene converters useful in stage 210 will now be described in more detail, although the invention is not limited thereto, and this description is not meant to foreclose other acetylene conversion embodiments within the broader scope of the invention.

In an embodiment, stage 210 includes at least one acetylene converter operated under adiabatic acetylene conversion conditions, the converter including at least one bed of an acetylene conversion catalyst.

Conventional acetylene conversion catalysts can be used in the catalyst bed(s) of stage 210, but the invention is not limited thereto. For example, suitable catalysts include those comprising 0.1 wt. % of one or more elements from Groups Ia, Ib, IIb, and/or VIII of the Periodic Table based on the weight of the catalyst, e.g., platinum, nickel, and/or palladium. Optionally, the catalyst further comprises a support, e.g., a support comprising 0.1 wt. % (based on the weight of the catalyst) of at least one inorganic oxide composition such as alumina, silica, and/or silica-alumina. For example, in one embodiment the catalyst comprises a supported catalyst comprising one or more of platinum, nickel, and/or palladium, including those which further comprise silver and/or zinc. Optionally, the catalyst comprises i) ≥0.1 wt. % of at least one of palladium, nickel, or zinc, and (ii) ≥0.1 wt. % of at least one inorganic oxide, the weight percents being based on the weight of the acetylene conversion catalyst. Optionally, the catalyst has one or more of a bulk density in the range of 0.16 g/cm$^3$ to 1.60 g/cm$^3$ (10.0 pounds per cubic foot to 100.0 pounds per cubic foot), a loss on ignition at 538° C. (1000° F.) of ≤10.0 wt. % based on the weight of the catalyst, a crush strength ≥22 Newtons (5.0 pounds), a surface area ≥0.1 m$^2$/gram, a particle size (largest dimension) ≥0.1 mm, and a pore volume ≥0.01 cm$^3$/g.

The acetylene converter of stage 210 can be operated at adiabatic acetylene conversion conditions that include one or more of a Gas Hourly Space Velocity ("GHSV") in the range of $1.0 \times 10^2$ to $1.0 \times 10^5$, a pressure in the range of 1.0 bar to 100.0 bar, and an average bed temperature (start of run) in the range of 50° C. to 125° C.

In an embodiment, stage 210 includes at least one adiabatic, front-end acetylene converter for deriving the first product from the third mixture, the third mixture having a molecular hydrogen:acetylene molar ratio ≥3.0. e.g., in the range of 10.0 to 40.0, and a carbon monoxide to acetylene molar ratio in the range of 0.01 to 1.5; the third mixture comprising $A_2$ wt. % of acetylene and $A_3$ wt. % of ethylene based on the weight of the third mixture; the product comprising $A_5$ moles of acetylene and $A_6$ moles of ethylene based on the weight of the product; and wherein $A_6 \geq A_3$, $A_5 < A_2$, and $(A_6-A_3)(A_2-A_5) \geq 0.50$. Optionally, in front-end acetylene conversion embodiments, the third mixture comprises >0.1 wt. % $C_{3+}$, e.g., the range of 0.5 wt. % to 2.0 wt. % $C_{3+}$ based on the weight of the third mixture.

In an embodiment, the acetylene converter of stage 210 is front-end acetylene conversion utilizing at least one isothermal acetylene converter. An isothermal temperature can be maintained within the converter, e.g. by the vaporization of a diluent such as methanol, the heat generated by acetylene conversion being moderated by the methanol's latent heat of vaporization. The acetylene catalyst can be the same as those described for adiabatic acetylene converters.

The acetylene converter of stage 210 can be operated at isothermal acetylene conversion conditions that include one or more of a space velocity ("GHSV") in the range of $1.0 \times 10^2$ to $1.0 \times 10^5$, a pressure in the range of 1.0 bar to 100.0 bar, and an average bed temperature (start of run) in the range of 50° C. to 125° C.

Stage 210 can include front-end acetylene conversion that includes at least one isothermal acetylene converter for deriving the first product from the third mixture, the third mixture having a molecular hydrogen:acetylene molar ratio ≥3.0. e.g., in the range of 10.0 to 40.0 and a carbon monoxide to acetylene molar ratio in the range of 0.01 to 1.5; the third mixture comprising $A_2$ weight percent of acetylene and $A_3$ weight percent of ethylene based on the weight of the third mixture; the product comprising $A_5$ weight percent of acetylene and $A_6$ weight percent of ethylene based on the weight of the product; and wherein $A_6 \geq A_3$, $A_5 < A_2$, and $(A_6-A_3)/(A_2-A_5) \geq 0.50$. Optionally, in front-end acetylene conversion embodiments, the third mixture comprises >1.0 wt. % $C_{3+}$, e.g., in the range of 2.0 wt. % to 20.0 wt. $C_{3+}$ based on the weight of the third mixture.

Stage 210 can include at least one back-end acetylene converter operated under adiabatic and/or isothermal acetylene conversion conditions, the converter including at least one bed of acetylene conversion catalyst. The isothermal acetylene converter(s), adiabatic acetylene converter(s), operating conditions used therein, acetylene conversion catalyst(s), etc., can be the same as those described for front-end acetylene conversion. Optionally, the third mixture utilized for back-end acetylene conversion contains acetylene in a relative amount ≥ than that utilized in front-end acetylene conversion, the difference resulting from, e.g., separations of hydrogen, methane, $C_{3+}$, acid gases such as $CO_2$, etc., as might occur in upgrading stage 208. For example, the third mixture can comprise $C_{3+}$ hydrocarbon in an amount ≤1.0 wt. %, e.g. ≤0.01 wt. % based on the weight of the third mixture.

If desired, stage 210 can include means for separating from the acetylene converter's product one or more of methane, ethane, propane or species having a molecular weight ≥propane's, such as green oil. For example, such separations can be carried out after splitting step 212. Such means can include one or more of demethanizers, dethanizers, ethane/ethylene splitters, and/or separation equipment for processing the higher-molecular weight species. Although such means can be conventional, the invention is not limited thereto. Optionally, stage 210 includes at least two acetylene converters operated in parallel, with at least one converter being utilized for acetylene conversion and at least the second converter being subjected to catalyst regeneration. Optionally, stage 210 includes means for compressing at least a portion of the ethylene in the acetylene converter's effluent, e.g., conventional compressing. Optionally, the third mixture comprises at least a portion of ethylene derived from the first product, e.g. ≥10.0 mole % per mole of the third mixture, such as ≥25.0 mole %.

The process can include conducting away a first product from stage 210, the first product derived from at least a portion of the effluent of at least one of stage 210's acetylene converters. For example, the first product can comprise the effluent of a front-end and/or back-end acetylene converter of stage 210. Optionally, the third mixture comprises one or more of the following molecules derived from the first product: hydrogen, CO, ethylene, acetylene, methane, ethane, propane, molecules having a molecular weight ≥ than that of propane, etc.

Stage 210 can be a back-end acetylene conversion stage, the stage comprising. e.g., one or a plurality of acetylene converters, such as at least two acetylene converters operated in series. Upgrading stage 208 can be utilized upstream of stage 210. Dividing means (stage 212), e.g., a splitter, can be utilized downstream of stage 210 to recycle a divided portion of the third product to combining means (stage 209). Stage 209 can be located downstream of upgrading stage 208 and upstream of acetylene conversion stage 210. Stage 212 can be utilized for dividing (e.g., splitting) the first product into two portions: (i) a first portion which can be, e.g., conducted to stage 214 for polymerization of at least a portion of the first portion's ethylene and (ii) a second portion for recycle to stage 209, wherein the third mixture is derived from the second mixture by combining the second portion of the first product with the upgraded second mixture conducted away from upgrading stage 208. For example, the second portion of the first product can comprise ≥10.0 wt. %, e.g., ≥50.0 wt. %, such as ≥90.0 wt. % of the first product, based on the weight of the first product. Optionally, the second portion of the first product comprises 40.0 wt. % to 95.0 wt. % of the first product, based on the weight of the first product.

In one or more embodiments, stage 210 is a back-end acetylene conversion stage, where the third mixture has a carbon monoxide to acetylene molar ratio in the range of 0.01 to 1.5 and comprises $A_1$ moles of saturated hydrocarbon, $A_2$ moles of acetylene, and $A_3$ moles of ethylene per mole of the third mixture; the first product comprises $A_4$ moles of saturated hydrocarbon, $A_5$ moles of acetylene, and $A_6$ moles of ethylene per mole of the product; wherein $A_6 \geq A_3$, $A_5 < A_2$, and $(A_6-A_3)/(A_2-A_5) \geq 0.5$. For example, the third mixture can have a molecular hydrogen:acetylene molar ratio ≥1.0, e.g., in the range of 1.0 to 5.0, and $1.0 \times 10^3$ ppmm to $2.5 \times 10^4$ ppmm of carbon monoxide; wherein (i) $A_2$ is ≥0.5 wt. %, e.g., in the range of from about 1.0 wt. % to about 10.0 wt. %, such as 2.0 wt. % to 6.0 wt. % based on the weight of the third mixture, and (ii) $A_3$ is ≥25.0 wt. %, e.g., in the range of from about 30.0 wt. % to about 90.0 wt. % based on the weight of the third mixture. The balance of the third mixture (to total 100.0 wt. %) can comprise, e.g., saturates, molecular hydrogen and/or diluent. The values of $A_5$ and $A_6$ can be, e.g., $A_5 < 0.05$ wt. %. e.g., in the range of from about 0.0 wt. % to about 0.10 wt. %, such as 0.0 wt. % to 0.001 wt. % based on the weight of the first product; and $A_6 > 25.0$ wt. %, e.g., in the range of from about 30.0 wt. % to about 90.0 wt. %, e.g., 40.0 wt. % to 85.0 wt. % based on the weight of the first product. The balance of the first product (to total 100.0 wt. %) can comprise, e.g., saturates, molecular hydrogen and/or diluent.

Optionally, at least a first portion of the first product is polymerized in stage 214 to form a second product comprising, e.g., polyethylene. Conventional polymerization processes can be used, including those utilizing one or more comonomers with the propylene, but the invention is not limited thereto.

The process can utilize a reverse-flow, regenerative pyrolysis reactor system for at least a portion of the pyrolysis of stage 206. An example of such a process within the scope of the invention will now be described in more detail. The following description is not meant to foreclose other embodiments within the broader scope of the invention.

V. Particular Embodiment Utilizing a Reverse-flow, Regenerative Pyrolysis Reactor In an embodiment, the invention relates to a hydrocarbon conversion process comprising exposing a first mixture to a temperature $\geq 1.40 \times 10^{3\circ}$ C. at a total pressure ≥0.10 bar (absolute) in a first region of a reverse-flow, regenerative pyrolysis reactor and conducting away from the first region at least a portion of a second mixture, the second mixture being derived from the first mixture by the pyrolysis. The process for deriving the second mixture from the first mixture is generally endothermic, and can be conducted, e.g. under the high-severity thermal pyrolysis conditions described in Section II. The first mixture comprises hydrocarbon and oxygenate. When operated under these pyrolysis temperatures and pressures, the second mixture has a carbon monoxide to acetylene molar ratio in the range of $2.5 \times 10^{-3}$ to 1.0 and comprises ≥1.0 wt. % $C_2$ unsaturates based on the weight of the second mixture. The process further comprises exothermically reacting at least a portion of first and second reactants of a fourth mixture in a second region of the reverse-flow, regenerative pyrolysis reactor to produce a fifth mixture. The exothermic reacting of the fourth mixture's first and second reactants provides at least a portion of the heat utilized in the first region for deriving the second mixture from the first mixture. The first and second regions can be at least partially coextensive, for example, and the exothermic reacting of the fourth mixture's reactants can be conducted at a substantially different time than the pyrolysis.

In the illustrative embodiment shown in FIG. 2, stage 206 comprises a reverse-flow, regenerative pyrolysis reactor. In accordance with this embodiment, the first mixture is conducted to a first region (2064) of the reverse-flow, regenerative pyrolysis reactor via at least one conduit (2046). The first and second reactants of the fourth mixture are conducted to a second region (2063) of the reactor via conduit 305. The first and second reactants are conducted to region 2063 through separate channels within conduit 305, the first and second reactants being combined to produce the fourth mixture (for the exothermic reaction) in proximity to the downstream end of conduit 305 and the upstream end of region 2063. In another embodiment, the first reactant is conducted to region 2063 via conduit 305, with the second reactant being conducted to region 2063 via a second conduit (3051—not shown).

The first and second regions are at least partially coextensive as shown. The first mixture is derived from one or more source materials (200), e.g., natural gas, air, etc. Optionally, the one or more of the source materials are upgraded in optional preparation stage (204) to produce the first mixture. The fourth mixture comprises first and second reactants. The first reactant can comprise, e.g., ≥50.0 wt. % fuel based on the weight of the first reactant, such as ≥90.0 wt. % fuel, and the second reactant can comprise, e.g., >50.0 wt. % oxidant based on the weight of the second reactant, such as ≥90.0 wt. %. The fuel can be derived from at least one second source material (300), e.g., natural gas, petroleum, other hydrocarbon, etc., including fractions, products, or byproducts thereof. The oxidant can comprise, e.g., oxygen, etc., and can be derived, e.g. from a source material (not shown) such as air. Optionally, one or more of the fourth mixture's source materials is upgraded in a second preparation stage (302) upstream of conduit 305 and optional conduit 3051 (not shown). Stage 302 can optionally include one or more of separation, conversion, addition of recycled portions of the second and/or fifth mixtures, etc. In this embodiment, the reactor 206 is (i) "reverse flow" in the sense that upstream region of the reactor with respect to the first mixture is the downstream region with respect to the fourth mixture and (ii) "regenerative" in the sense that at least a portion of the heat consumed during the conversion of the first mixture is provided by oxidizing the fourth mixture.

Continuing with the illustrative embodiment of FIG. 2, fuel is conducted via a first channel (or plurality thereof) in conduit 305 and oxidant is conducted via a second channel (or plurality thereof) in conduit 305 or optionally via a second conduit 3051 (not shown) to the second region 2063. Although the invention is described in terms of a fourth mixture comprising fuel and oxidant, the invention is not limited thereto, and this description is not meant to foreclose other first and second reactants within the broader scope of the invention. Optionally at least a portion of conduit 305 (and/or conduit 3051 when utilized) is located within the reactor of stage 206.

Proximate to the downstream end of conduits 305 (or 305 and 3051), the fuel and oxidant are combined to produce the fourth mixture, the fuel and oxidant then react exothermically in the second region 2063 (the flow of the first and second reactants and the products thereof being represented by dashed line 2062). The exothermic reaction provides at least a portion of the heat utilized in the coextensive portion of region 2064 during the pyrolysis. The fifth mixture, comprising at least a portion of the compositions resulting from the reaction of the fourth mixture's fuel and oxidant (and optionally including a portion of the fourth mixture that is not consumed in the reaction), is conducted away from stage 206 via a conduit (2066). Optionally at least a portion of conduit 2066 is located within the reactor of stage 206.

After at least a portion of the fourth mixture's fuel and oxidant are exothermically reacted in region 2063 (e.g., by an oxidation reaction such as combustion), the first mixture is conducted to the upstream end of region 2064 via conduit 2046. Optionally at least a portion of conduit 2046 is located within the reactor of stage 206. The first mixture traverses region 2064 (the traversal being represented by solid line 2061), abstracting heat from region 2064 to pyrolyse the first mixture in order to produce the second mixture. In this embodiment, at least a portion of the heat abstracted by the first mixture in region 2064 is produced in region 2063 by the reaction of the first and second reactants. Optionally, a major amount of the heat abstraction occurs in the portion of region 2064 that is coextensive with region 2063. The second mixture is conducted away from stage 206 via at least one conduit (2065). Optionally at least a portion of conduit 2065 is located within the reactor of stage 206. In an embodiment, conduit 2065 comprises at least a portion of the channels within conduit 305; which can serve, e.g., to preheat the fuel and/or oxidant of the fourth mixture before combustion.

Optionally, after at least a portion of the second mixture is conducted away from region 2064, the fuel and oxidant utilized to produce the fourth mixture are again conducted through separate channels within conduit 305 to region 2063, and the process repeats in sequence—exothermically reacting the fuel and oxidant of the fourth mixture to heat the reactor and then utilizing at least a portion of the heat for pyrolysing the first mixture. The process can thus be operated sequentially. e.g., continuously, semi-continuously, or even in batch mode. Optionally, stage 206 comprises a plurality of pyrolysis reactors operating, e.g., in series, parallel, or a combination thereof.

Continuing with the illustrative embodiment of FIG. 2, the first product is conducted away from conversion stage 210 via a conduit (2101) to stage 212 containing dividing means (e.g., a splitter). The dividing means convey a second portion of the first product away from a first portion. The second portion, which comprises ethylene, carbon monoxide, and optionally saturated hydrocarbon, hydrogen, and carbon monoxide, is conducted to stage 209 via at least one conduit (2121). Stage 209 comprises means for combining the second portion of the first product with the portion of the second mixture conducted away from stage 208 via conduit 2081, e.g., valve means, to produce the third mixture.

An optional second conversion stage (214), can be utilized for converting at least a portion of the first portion of the first product to a second product comprising polyolefin, e.g., polyethylene, which can be conducted away via conduit 2141. Optionally, the process further includes one or more of the following components: a second upgrading stage (308) for upgrading the fifth mixture downstream of conduit 2066; one or more conduits for adding to the fourth mixture's fuel source materials one or more of light saturated hydrocarbon such as methane (3001) or oxygenate (3002); conduits for adding to the fourth mixture's oxidant source material(s) additional or supplemental oxidant (3003); one or more conduits for adding to the first source material one or more of molecular hydrogen (2043); hydrocarbon, e.g., light saturated hydrocarbon such as methane (2044), or oxygenate (2045); conduits for conducting hydrogen (2042) to preparation stage 204 and for conducting away heteroatom species such as hydrogen sulfide or non-volatiles (2041); one or more conduits for conducting away a first byproduct from upgrading stage 308, the first byproduct including at least one of non-oxidized hydrocarbon (3081) and/or oxygenate (3082); a conduit (3083) for conducting heteroatom species such as $NO_x$, $SO_x$, $CO_2$, $N_2$, sulfuric acid, etc. away from upgrading stage 308; one or more conduits for conducting a second byproduct away from stage 208, the second byproduct including at least one of molecular hydrogen (2082) or light saturated hydrocarbon (2083); one or more conduits for conducting away non-volatiles (2084) and/or heteroatom species such as hydrogen sulfide (2085) away from upgrading stage 208; or one or more conduits (not shown) for adding to the second mixture one or more of (i) hydrogen; (ii) methane, ethane, and/or other light saturated hydrocarbon, or (iii) ethylene. In an embodiment, (a) the first, second, and third mixtures are substantially the same as those described in sections I and III and (b) stages 204, 206, 208, 209, 210, 212, and 214 operate substantially the same way as described in sections II, IV, and V. The fourth and fifth mixtures will now be described in more detail.

VI. Fourth and Fifth Mixtures

Exothermically reacting the first and second reactants can provide at least a portion of the heat utilized by the pyrolysis. For example, the first and second reactants can be mixed within a pyrolysis reactor to produce a fourth mixture, the first and second reactants then reacting, e.g., by an oxidation reaction such as combustion, as the fourth mixture traverses at least a portion of the pyrolysis reactor. The first and second reactants can also be combined upstream of the pyrolysis reactor, with at least a portion of the first and second reactants exothermically reacting within the pyrolysis reactor. The first reactant can comprise, e.g., fuel such as molecular hydrogen, synthesis gas (mixtures of CO and $H_2$), or hydrocarbon, such as ≥10.0 wt. % hydrocarbon (including mixtures thereof), or ≥50.0 wt. % hydrocarbon, or ≥90.0 wt. % hydrocarbon based on the weight of the first reactant. The second reactant can comprise e.g., ≥10.0 oxidant, e.g., or ≥50.0 wt. % oxidant, or ≥90.0 wt. % oxidant based on the weight of the second reactant. Optionally, the fourth mixture further comprises diluent. When the first reactant comprises hydrocarbon, the particular hydrocarbon selected is not critical. For example, in an embodiment, the hydrocarbon comprises one or more of the hydrocarbons specified for the first mixture, e.g., methane. In an embodiment, the hydrocarbon is derived from, comprises, consists essentially of or consists of one or more of Fischer-Tropsch gases, methane, methane containing streams such as coal bed methane, biogas, associated gas, natural gas and mixtures or components thereof. When the first reactant comprises hydrogen and/or hydrocarbon and the second reactant comprises oxidant, the choice of oxidant is not critical, provided the oxidant is capable of exothermically reacting with the hydrogen and/or hydrocarbon. For example, in an embodiment, the oxidant comprises, e.g., molecular oxygen and/or ozone.

Referring to FIG. 2, in cases where the fuel source material(s) 300 are too lean in one or more of hydrocarbon (e.g., light hydrocarbon such as methane), hydrogen, or diluent, these can be added through one or more of conduits 3001 or 3002. When oxidant source materials do not contain sufficient oxygen or ozone, either or both of these can be added to stage 302 via one or more conduits (3003). For example, in some embodiments it is beneficial to increase the amount of oxidant in the fourth mixture beyond that needed to oxidize substantially all of the fourth mixture's fuel, e.g., in embodiments where the pyrolysis of the first mixture deposits a hydrocarbon-containing residue in the pyrolysis reactor and the process would benefit from oxidizing at least a portion of the residue. In other embodiments, it is beneficial to lessen the amount of oxidant in the fourth mixture, e.g., when it is desired to conduct the oxidizing of the fourth mixture under partial oxidation conditions. In still other embodiments, it is beneficial for the fourth mixture to contain a substantially stoichiometric amount of oxidant, i.e., the amount of oxidant needed to oxidize substantially all of the fourth mixture's fuel.

Optionally, the fourth mixture further comprises diluent, e.g., ≥1.0 wt. % of diluent based on the weight of the first mixture. Suitable diluents (which can be a diluent mixture) include one or more of, e.g., water, carbon dioxide, non-combustible species, nitrogen ($N_2$), hydrogen sulfide, $C_{4+}$ mercaptans, amines, mixtures of amines, non-hydrocarbon non-volatiles (whether combustible or not) including refractory inorganics such as refractory oxygenates, inert gas (including inert gas mixtures), etc. In an embodiment, the fourth mixture comprises ≤96.0 wt. % diluent, e.g., in the range of 65.0 wt. % to 94.5 wt. % diluent, based on the weight of the fourth mixture.

In an embodiment, the fourth mixture comprises ≥1.0 wt. % molecular oxygen, e.g., in the range of 5.0 wt. % to 25.0 wt. %, such as 7.0 wt. % to 15.0 wt. %; ≥0.1 wt. % fuel, e.g., in the range of 0.5 wt. % to 10.0 wt. %, such as 1.0 wt. % to 5.0 wt. %, the weight percents being based on the weight of the fourth mixture, with the balance of the fourth mixture being diluent.

The fifth mixture comprises (i) products derived from the exothermic reaction of the fourth mixture's first and second reactants, (ii) diluent, when diluent is present in the fourth mixture, and optionally (iii) unreacted first and/or second reactants. When the exothermic reaction of the first and second reactants involves hydrocarbon combustion, or when a diluent is present in the fourth mixture (such as $N_2$ or $H_2S$), the fifth mixture can comprise carbon dioxide, and can further comprise sulfur oxides, nitrogen oxides, etc.

A continuous or semi-continuous process for deriving (a) the second mixture from the first mixture and (b) the fifth mixture from the fourth mixture will now be described in more detail. Although the process is described in terms of a reverse-flow, regenerative pyrolysis reactor, the invention is not limited thereto, and this description is not meant to foreclose other embodiments within the broader scope of the invention.

VII. Continuous or Semi-Continuous Process

Referring to FIG. 2, the first reactant is conducted via one or more first channels within conduit 305 and the second reactant is conducted via one or more second channels within conduit 305 or optionally via a second conduit 3051 (not shown). The first and second reactants are thus conducted separately to the upstream end of region 2063, where the first and second reactants are combined to form the fourth mixture. A fifth mixture, derived from the exothermic reacting (combustion) of at least a portion of the fourth mixture's first and second reactants in region 2063 is conducted away from stage 206 via conduit 2066. At least a portion of the heat of combustion is utilized to increase the temperature of region 2064. At the conclusion of the combustion step, the fifth mixture is conducted away via conduit 2066 and the first mixture is introduced into the reactor (optionally after an optional purge of the fifth mixture from stage 206 by a non-reacting material such as an inert purge gas). The relative types and amounts of the first and second reactants are selected so that the (exothermic) heat of reaction obtained during the reaction sufficiently heats region 2064, particularly the portion of region 2064 that is coextensive with region 2063, for exposing the first mixture to a temperature ≥1.40×10³° C.

Pyrolysis reactor of stage 206 can be, e.g., one or more of the pyrolysis reactors described in U.S. Patent App. Pub. No. 2007/0191664. For example, the reactors of that reference provide a high-temperature heat bubble formed in the middle of a packed-bed reactor system. The reactor system can be utilized in a two-step process wherein heat is (1) added to the bed via in-situ combustion (e.g., of the fourth mixture) and then (2) removed from the bed via pyrolysis (e.g., in-situ endothermic reforming of the first mixture). For example, in one embodiment the reactor system comprises two reactors: (a) a first (heat recuperating) reactor and (b) a second (pyrolysis) reactor. Deriving the second mixture from the first mixture in such a system does not require a catalyst, though one can be used, e.g., to optionally convert light hydrocarbon (e.g., methane) in the first mixture to acetylene.

The reactor system can be operated, e.g., in series, parallel, or a combination thereof, and utilizes accompanying valve means for conducting the first-fifth mixtures to/from the reactors of the reactor system. For example, in one embodiment reactor system includes first and second reactors, oriented in a series relationship with each other with respect to a common flow path, optionally along a common axis. The common axis may be horizontal, vertical, or some other orientation with respect to the surface of the earth.

Optionally conduits 305 and 3051 include segments which are in the form of separate but substantially parallel channels located within a quenching reactor bed (e.g., the first reactor), the first reactor being located within stage 206. In other words, the first and second reactants can be conducted toward the second reactor via substantially independent flow paths (e.g., the first reactor can be a ceramic article with channels located therein). Optionally, the first and/or second reactants abstract heat from the first reactor. Optionally, other components utilized to produce the fourth mixture, e.g. diluent, can be conducted through the first reactor together with the first reactant, the second reactant, or a portion with each. When the components utilized to produce the fourth mixture (optionally heated by the hot first reactor) reach a designated location within the reactor system, the components are combined and at least a portion of the fourth mixture's first reactant exothermically reacts with at least a portion of the fourth mixture's second reactant in region 2063.

The combustion can result in a high temperature zone (also referred to by those skilled in the art as a temperature bubble), at least a portion of the temperature bubble being located in region 2063 and having a temperature $\geq 1.50 \times 10^{3\circ}$ C., e.g., in the range of about $1.60 \times 10^{3\circ}$ C. to about $1.70 \times 10^{3\circ}$ C. Optionally, the combustion completely oxidizes the oxidizable species (e.g., fuel) in the first reactant, including hydrocarbon, hydrogen. etc. therein. Optionally, diluent such as nitrogen that may be present in the fourth mixture is not oxidized to a significant extent. Optionally, $\geq 50.0\%$ of the combustion (based on the amount of the fourth mixture, mole basis, that is oxidized in region 2063), e.g., $\geq 75.0\%$, such as $\geq 90.0\%$ of the combustion occurs in the portion of region 2063 that is located between the first and second reactors. Optionally, the combustion duration is for a time sufficient for the second reactor to abstract heat from the combustion, the second reactor being located at least partially within zone 2063 but downstream of the first reactor with respect to the flow of the fourth mixture. In other words, the combustion optionally displaces the temperature bubble into and at least partially through the second reactor. For efficiency, it is generally undesirable to displace the temperature bubble past the downstream end (with respect to the flow of the fourth and fifth mixtures) of the second reactor, e.g., to avoid waste of heat and/or overheating the second reactor. In an embodiment, the fifth mixture, derived from the combustion of the fourth mixture, is conducted through the second reactor and away from stage 206.

Optionally, the total amount of heat added to the reactor system during the exothermic reaction of the first and second reactants (e.g., the regeneration step) does not exceed the sum of the heats that are required (a) to sustain the pyrolysis reaction for endothermically driving the second mixture from the pyrolysis portion of the first mixture and (b) for heat losses from the system, e.g., by as conduction losses through reactor walls and/or convective losses with, e.g., the second mixture. Optionally, the total amount of heat stored in the reactor system though is generally much more than the minimum amount of heat needed for the pyrolysis in any single cycle of a continuous or semi-continuous process.

After at least a portion of the fourth mixture's hydrocarbon has been oxidized, the pyrolysis portion of the first mixture is conducted to the upstream end of region 2064, e.g., the upstream end of the second reactor, where upstream is now defined with respect to the flow of the first and second mixtures. Optionally, a reactor purge can be used between the oxidation and pyrolysis steps. Optionally, the first mixture is exposed to a temperature $\geq 1.50 \times 10^{3\circ}$ C. under high severity thermal pyrolysis conditions, e.g., in the portion of region 2064 that is coextensive with region 2063 via proximity to the second reactor and other reactor internals (e.g., mixer media) located, e.g., in the temperature bubble region, which have been heated by the exothermic reaction of the first and second reactants. Optionally, at least a portion of the temperature bubble region is located within the portion of zone 2064 that is coextensive with zone 2063. Optionally an inert gas sweep is used before the combustion and/or pyrolysis steps of the process.

Figure 3A:
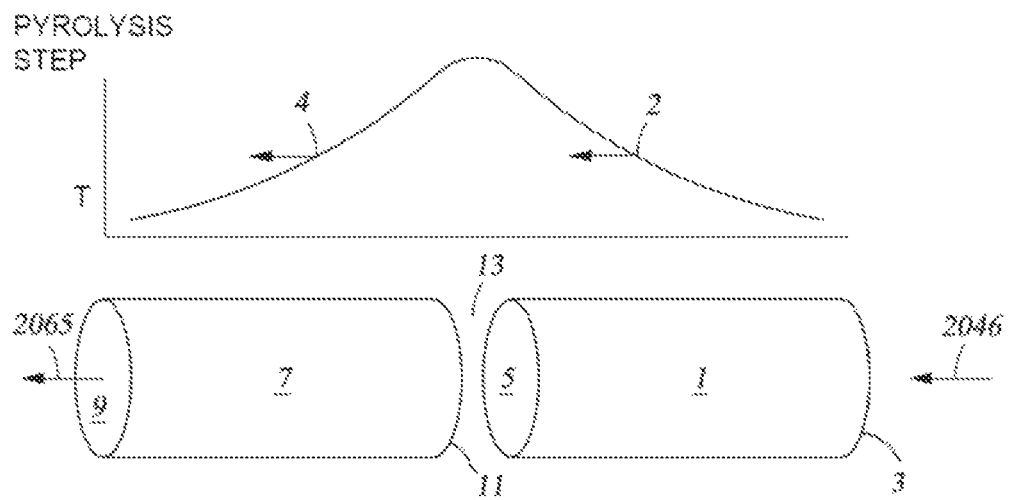
FIGS. 3A and 3B schematically illustrate a reverse-flow pyrolysis reactor's temperature profile.
Figure 3B:
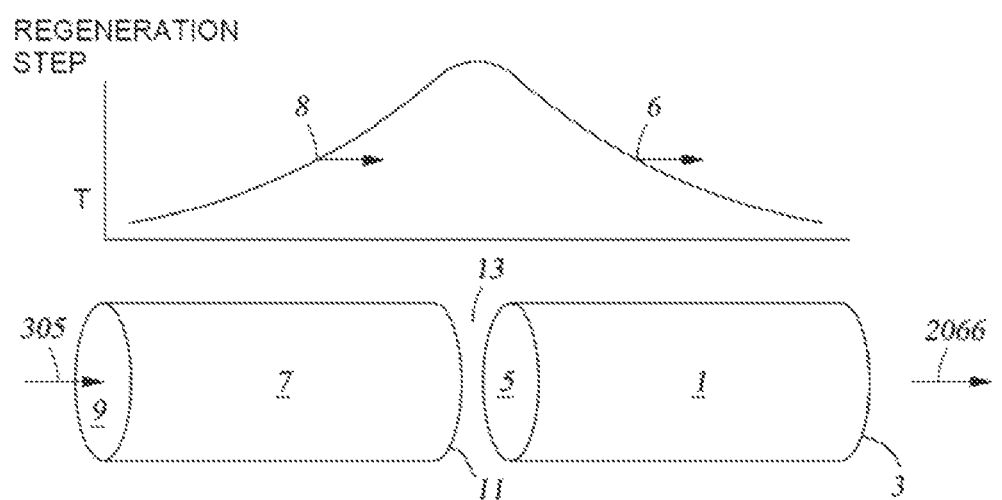

In one or more embodiments, stage 206 includes a reactor system shown schematically in FIGS. 3a and 3b. Referring now to FIG. 3, the reactor system comprises two reactors: a first (recuperator/quenching) reactor (7) and a second (pyrolysis) reactor (1). Optionally, the first and second reactors both contain regenerative beds, where the term "regenerative bed" means a reactor bed comprising materials that are effective in storing and transferring heat, and optionally useful for carrying out a chemical reaction. The regenerative beds comprise bedding or packing material such as glass or ceramic beads or spheres, metal beads or spheres, ceramic (including, e.g., alumina, yttria, zirconia, etc., and mixtures thereof) or metal honeycomb materials, ceramic tubes, extruded monoliths, catalysts, etc. Optionally, the materials comprising the regenerative bed maintain integrity, functionality, and withstand long term exposure to temperatures in excess of 1200° C., preferably in excess of 1500° C., more preferably in excess of 1700° C., and even more preferably in excess of 2000° C. for operating margin.

Figure 2B:
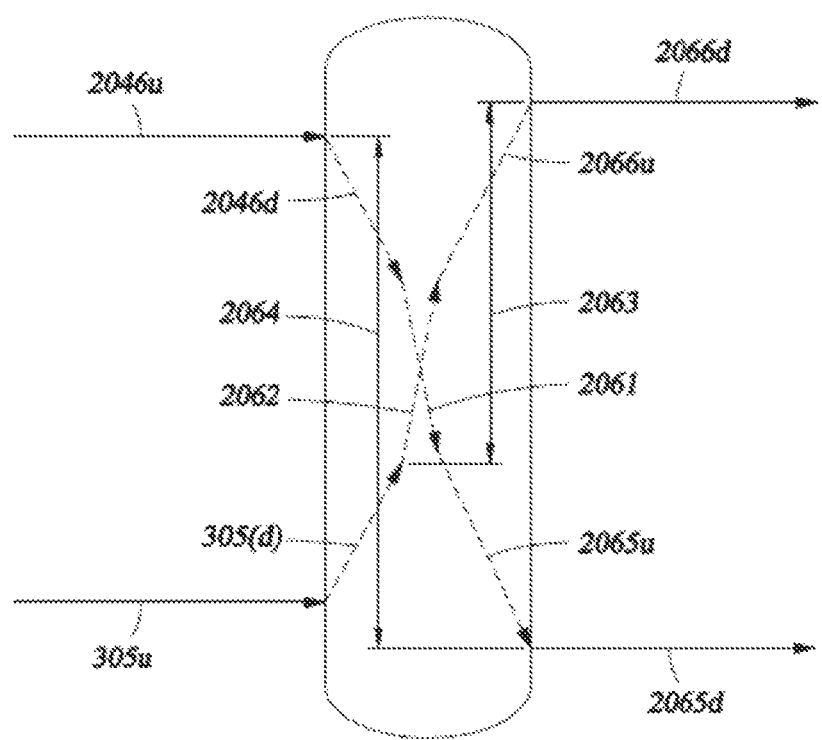

The continuous or semi-continuous process begins with "pyrolysis" step wherein (a) the downstream end (5) of the second reactor (1) (downstream with respect to the flow of the first mixture, as schematically shown in FIG. 3a) is at temperature greater than that of the upstream end (3) and (b) at least a portion (including the downstream end (9)) of the first reactor (7) is at a temperature less than that of the downstream end of the second reactor (5) in order to provide a quenching effect for the second mixture. The first mixture is conducted to the upstream end (3) of the second reactor via conduit 2046. Optionally, conduit 2046 comprises upstream (2046u) and downstream segments (2046d), as shown in FIG. 2b. Upstream segment 2046u (represented in the figure by a solid line) is external to the second reactor (1). Downstream segment 2046d (represented by a dashed line), is in fluid communication with 2046u and is located within second reactor (1), e.g., as one or more channels within the reactor.

Continuing with reference to FIG. 3a, the first mixture abstracts heat from the first reactor, resulting in the derivation of the second mixture from the first by pyrolysis. As this step proceeds, a shift in the temperature profile (2) occurs (e.g., a shift in the trailing edge of the temperature bubble as indicated by the arrow), the amount of this shift being influenced by, e.g., the heat transfer properties of the system. At least a portion of the second mixture, e.g., the portion in the vapor phase, is conducted from the downstream end (5) of the second reactor to the upstream end (11) of the first reactor (7), and is conducted away from the first reactor via conduit 2065 proximate to the downstream end (9), as shown. Optionally, conduit 2065 comprises upstream (2065u) and downstream segments (2065d), as shown in FIG. 2b. Downstream segment 2065d (represented in the figure by a solid line) is external to the first reactor (7). Upstream segment 2065u (represented by a dashed line), is in fluid communication with 2065u and is located within the first reactor (7), e.g., as one or more channels within the reactor. At the start of pyrolysis, the first reactor (7) has a temperature less than that of the second reactor (1). As the second mixture traverses the first reactor (7), the second mixture is quenched (e.g., cooled) to a temperature approaching that of the downstream end (9) of the first reactor. As the second mixture is quenched in the first reactor (7), the leading edge of the temperature profile (4) moves toward the downstream end (9) of the first reactor (7). In at least one of the embodiments represented by FIG. 3a, the upstream end of pyrolysis region 2064 (referenced in FIG. 2) is proximate to the upstream end (3) of the second reactor (1). The downstream end of pyrolysis region 2064 is proximate to the downstream end (9) of the first reactor (7). Since the quenching heats the first reactor (7), the combustion step optionally includes cooling the first reactor, e.g., to shift the leading edge of the temperature profile away from end (9) of the first reactor (7), as illustrated schematically in FIG. 3b.

The pyrolysis step can be operated for a time duration $t_1$ in the range of $1.0 \times 10^{-3}$ seconds to 10.0 seconds. Optionally, the pyrolysis step includes one or more of the following conditions: the first mixture achieves a peak pyrolysis gas temperature $\geq 1.40 \times 10^{3\circ}$ C., e.g., in the range of $1.45 \times 10^{3\circ}$ C. to $2.20 \times 10^{3\circ}$ C., such as, $1.50 \times 10^{3\circ}$ C. to $1.90 \times 10^{3\circ}$ C., or $1.60 \times 10^{3\circ}$ C. to $1.70 \times 10^{3\circ}$ C.; a total pressure $\geq 1.0$ bar (absolute). e.g., in the range of 1.0 bar to about 15 bar, such as in the range of 2.0 bar to 10.0 bar; and/or a high-severity residence time $\leq 0.1$ seconds, e.g., $\leq 5.0 \times 10^{-2}$ seconds, such as $\leq 5.0 \times 10^{-3}$ seconds. Optionally, the first mixture comprises $\geq 0.01$ mole % of hydrocarbon, e.g., 0.1 mole % to 90.0 mole % of hydrocarbon; $\geq 200.0$ ppmm of oxygenate, e.g., 500.0 ppmm to $3.0 \times 10^4$ ppmm of oxygenate; and $\geq 0.01$ mole % of molecular hydrogen. e.g., 0.1 mole % to 90.0 mole % of molecular hydrogen, the mole percents being based on the sum of the number of moles of hydrocarbon, oxygenate, and hydrogen in one mole of the first mixture. Optionally, the oxygenate comprises carbon dioxide and/or carbon monoxide, e.g., >90.0 wt. % carbon monoxide based on the weight of the oxygenate. When an oxygenate other than carbon monoxide is utilized or when the oxygenate is a mixture, the amount of oxygenate is as specified in the description of the first mixture. When it is desired to increase the amount of one or more of molecular hydrogen, hydrocarbon (e.g. light saturated hydrocarbon such as methane), and oxygenate in the first mixture, these can be added (e.g., in stage 204) as follows:

(i) Molecular hydrogen can be added via conduit 2043, with the added hydrogen obtained, e.g., from one or more of (a) from the process via conduit 2082 when optional stage 208 is present, (b) from molecular hydrogen separated from the first product, or (c) from an external source.

(ii) Hydrocarbon can be added via conduit 2044. These species can be obtained from the process via conduit 3081 or 2083, e.g., when optional stages 308 and 208 are utilized, from hydrocarbon separated from the first product, or from an external source.

(iii) Oxygenate can be added via conduit 2045. The oxygenate can be obtained, e.g., (a) from the process via conduit 3082, when optional stage 308 is utilized, (b) from carbon monoxide separated from the first product, (c) steam, e.g., steam generated in a process cooler, (d) carbon dioxide separated from the second mixture, and/or (e) from a source external to the process.

It is understood that flow control means (e.g. one or more of valves, rotating reactor beds, check valves, louvers, flow restrictors, timing systems, etc.) can be used to control gas flow, actuation, timing, and to alternate physical beds between the flow systems for the first, second, fourth, and fifth mixtures, and the optional purge gas when used. The combustion step will now be described in more detail, with reference to FIG. 3b.

The second step of the process, referred to as the combustion or regeneration step, begins by separately conducting first and second reactants to the first reactor (7), with the to term "upstream" now being with respect to the flow of the fourth mixture, as shown in FIG. 3b. The first and second reactants are conducted to first reactor (7) via conduit (or a plurality of conduits) 305 and optionally 3051 (not shown). The first reactant can be conducted via a first channel (or plurality thereof) located within conduit 305, and the second reactant is separately (and optionally simultaneously) conducted via a second channel (or plurality thereof) within conduit 305 or via a channel or plurality thereof in a second conduit 3051 (not shown). Optionally, conduit 305 comprises upstream (305u) and downstream segments (305d), as shown in FIG. 2b. Upstream segment 305u (represented in the figure by a solid line) is external to first reactor (7). Downstream segment 305d (represented by a dashed line), is in fluid communication with 305u and is located within first reactor (7), e.g., as one or more channels therein. When conduit 3051 is utilized to convey the second reactant, conduit 3051 can comprise upstream (3051u) and downstream (3051d) segments; 3051u and 3051d being in fluid communication, and wherein (a) 3051u is located external to first reactor (7) and (b) 3051d is located within first reactor (7), e.g., as one or more of a second set of channels therein, the first set of channels being those of conduit 305d. Conduits 305 and 3051 can include one or more spargers and/or distributors for conveying the first and second reactants from upstream segments 305u and 3051u into downstream segments 305d and 3051d. Suitable spargers, distributers, and configurations for using these to connect conduit segments are disclosed in U.S. Pat. No. 7,815,873; which is incorporated by reference herein in its entirety. Accordingly, the first and second reactants separately traverse first reactor (7) through their separate channels (in other words, the first and second reactants do not mix in the first reactor) and exit the downstream end (11) of the first reactor (7) where the first and second reactants are combined to produce a fourth mixture. The first and second reactants of the fourth mixture react exothermically at or proximate to a central region (13) of the reactor system. Optionally, the exothermic reaction continues downstream (with respect to the average flow of the fourth mixture) of region 13. e.g., in second reactor (1). Although this embodiment is described in terms of the first and second reactants separately traversing first reactor (7), the invention is not limited thereto, and this description is not meant to foreclose other embodiments within the broader scope of the invention, such as (a) embodiment where the first and second reactants are mixed to produce the fourth mixture, with the fourth mixture traversing reactor (7); or (b) embodiments where the first reactant is conducted into and through first reactor (7) via conduit 305 with the second reactant being conducted to region 13 via conduit 3051 by a path external to first reactor (7). The fifth mixture, comprising any unreacted fourth mixture and products resulting from the reaction of the first and second reactants, is conducted away from second reactor (1) via one or more conduits (2066). Optionally, conduit 2066 comprises upstream (2066u) and downstream segments (2066d), as shown in FIG. 2b. Downstream segment 2066d (represented in the figure by a solid line) is external to second reactor (1). Upstream segment 2066u (represented by a dashed line), is in fluid communication with 2066*d* and is located within the second reactor (1), e.g., as one or more channels within the reactor.

The combustion step thus includes the following features: (i) heating of region 13 and the second reactor (1) by transferring at least a portion of the heat of combustion to the reactor system downstream of the end (11) of the first reactor (7) and (ii) by transferring at least a portion of the sensible heat recovered from the first and second reactants from an upstream region of the first reactor (upstream with respect to the flow of the first and second reactants) toward one or more of the downstream region of the first reactor, region 13, or the second reactor in order to thermally regenerate the reactor system. Accordingly, the trailing edge (8) and leading edge (6) of the temperature profile translate downstream from their starting locations at the beginning of the combustion step, as shown in FIG. 3*b*.

As shown schematically in FIG. 3*b*, the exothermic reaction region 2063 can be located, e.g., between a first point proximate to the downstream end (11) of first reactor (7) and a second point proximate to the downstream end (3) of second reactor (1); "downstream" being with respect to the average flow of the fourth mixture. The pyrolysis region 2064 can be located, e.g., between a first point proximate to the upstream end (3) of the second reactor (1) and a second point proximate to the downstream end (9) of first reactor (7), "upstream" and "downstream" being with respect to the average flow of the first mixture. Referring now to FIG. 2*b*, it should be appreciated that the invention can be practiced without precisely defining (a) the boundaries of regions 2063 and 2064, (b) the precise locations of the intersections of flow-path 2062 with segments 305*d* and 2066*u*, or (c) the precise locations of the intersections of flow-path 2061 with segments 2046*d* and 2065*u* (the intersection locations being schematically depicted by inflections). Although region 2063 (the exothermic reaction region) is at least partially coextensive with pyrolysis region 2064, the upstream end of region 2063 ("upstream" with respect to the average flow of the fourth mixture) is proximate to the location where sufficient first and second reactants have combined to produce an exothermic reaction, this location being indicated in FIG. 2*b* as an inflection between segment 305*d* and flow-path 2062. The downstream end of region 2063 is generally proximate to the downstream end of second reactor (1) as shown in FIG. 2*b*, though this is not required, and in at least one embodiment the downstream end of region 2063 is located further downstream, e.g., in conduit 2066*d*. The intersection of flow-path 2062 (which encompasses at least a portion of region 13 and optionally, e.g. at least a portion of reactor (1)) with segment 305*d* (and 3051*d*) is generally proximate to the downstream end (11) of first reactor (7) (downstream with respect to the average flow of the fourth mixture), since that is where the first and second reactants combine. The practice of the invention does not require precisely defining the intersection of flow-path 2062 and segment 2066*u*. The practice of the invention does not require precisely defining the intersection of flow path 2061 (which encompasses at least a portion of region 13 and optionally, e.g., portions of reactors (1) and/or (7) and segments 2046*d* and 2065*u*). It should be recognized that the oscillatory translation of the leading and trailing edges of the temperature bubble during the combustion and pyrolysis steps confines the temperature bubble (which can achieve temperatures e.g., >1600° C.) to regions of the reactor system that can tolerate such conditions long-term.

If desired, at least a portion of the means utilized for conveying the first mixture into and through the first reactor, e.g., at least a portion of conduit 2046*d*, can also be utilized for conveying at least a portion of the fifth mixture, e.g., as conduit 2066*u*. In an embodiment, at least a portion of the means utilized for conveying the first and second reactants, e.g., at least a portion of conduit 305*d* (and/or 3051*d*), is also utilized for conveying at least a portion of the second mixture, e.g., via conduit 2065*u*.

Optionally, (a) segment 305*d* comprises a plurality of first channels (each channel, e.g., comprising an independent flow path) in the first reactor (7) and (b) segment 3051*d* comprises a plurality of second channels that may have the same or different cross sectional shape and size compared to those of the plurality of first channels. In one embodiment, the first reactor includes the first and second plurality of channels interdigitated in a honeycomb monolith structure. Honeycomb monoliths include, e.g., extruded porous structures such as those that are used for automotive catalytic converters, etc. The term "honeycomb" means a cross-sectional shape that includes multiple flow paths or conduits through the extruded monolith, but the use of this term is not meant to limit the monolith's structure or shape to any particular topology. In embodiments where a honeycomb monolith is used, the honeycomb monolith enables low pressure loss transference while providing contact time and heat transfer. Optionally, a mixer is used between the first and second reactors to improve combustion. Mixer means, distributer means, reactor system internals, valve means, etc. for the reactor system included in stage 206 can be substantially the same as those described in U.S. Patent App. Pub. No. 2007/0191664, for example.

The combustion step can be operated for a time duration greater than or equal to the time sufficient for heating pyrolysis region 2064 such that the first mixture is exposed to a temperature $\geq 1.4 \times 10^{3}$° C. during the pyrolysis step. The combustion step optionally includes one or more of the following conditions: a temperature $\geq 1.40 \times 10^{3}$° C., e.g., $\geq 1.50 \times 10^{3}$° C. such as $\geq 1.60 \times 10^{3}$° C., e.g., in the range of $1.90 \times 10^{3}$° C. to $2.20 \times 10^{3}$° C., and a pressure $\geq 1.0$ bar (absolute), e.g. in the range of 1.0 bar to 15.0 bar, such as 2.0 bar to 5.0 bar. Optionally, the combustion step oxidizes $\geq 97.0$ wt. % of the fourth mixture's fuel component, e.g., $\geq 99.0$ wt. %, based on the weight of the fourth mixture's fuel component. When it is desired to (a) increase the relative amount of one or more of hydrocarbon (e.g., methane) and/or hydrogen in the first reactant over that of the its source material or (b) increase the relative amount of oxidant (e.g., oxygen and/or ozone) in the second reactant over that of its source material, this can be done as follows:

(a) Hydrocarbon, such as light saturated hydrocarbon, e.g., methane, can be added via conduit 3001. These species can be obtained from (i) external sources and/or (ii) sources within the process such as from conduits 3081 or 2083, e.g., when optional stages 308 and 208 are utilized.

(b) Oxidant can be added via conduit 3003. The added oxidant can be obtained from (i) external sources and/or (ii) sources within the process such as from conduit 3082, e.g., when optional stage 308 is utilized and the oxygenate in conduit 3082 comprises oxidant. When the source material is air, the air can be obtained from a blower or compressor, for example.

Continuing with reference to FIG. 2, at the conclusion of the combustion step optional upgrading stage 308 can be used, e.g., to separate from the fifth mixture species that may be useful in other stages of the process. e.g., via conduits 3081-3083 as discussed, e.g., a low-$O_2$ diluent can be separated from the fifth mixture and utilized to produce the fourth mixture. The portion of the second mixture that is not used in other stages of the process can be conducted away from the process via one or more conduits (2087) for storage or further processing. At the conclusion of the pyrolysis step, optional upgrading stage 208 can be used, e.g., to separate from the second mixture species that may be useful in other stages of the process, e.g., via conduits 2082. Conventional separations processes are useful for stage 208 and 308, though the invention is not limited thereto. A third mixture is derived from the second mixture, e.g., in stages 208 and 209, and is conducted via conduit 2086 to conversion stage (210). In embodiments where downstream stages, e.g., acetylene conversion stage 210, polymerization stage 214, etc., operate at a higher pressure than the pyrolysis stage 206, means for increasing the second and, or third mixtures' pressure can be utilized, e.g., in stage 208 and locations downstream thereof. Conventional means for increasing pressure are suitable, e.g. one or more compressors, blowers, etc., though the invention is not limited thereto.

Stages downstream of stage 206, including optional stages, can be operated in the continuous process as specified above in section VI.

Example

The following prophetic example is conducted. A first mixture comprising 0.3329 moles of methane, 0.6658 moles of molecular hydrogen, and 0.0012 moles of carbon monoxide per mole of the first mixture is conducted to pyrolysis stage 206 and is isothermally exposed to a temperature of approximately 1500° C. at a total pressure of approximately 2.5 bar. 100.0 wt. % of the first mixture was subjected to the pyrolysis, and the conversion of the first mixture's methane is about 70%. The carbon monoxide has an Effectiveness Factor of approximately 1.0. In weight percents, the first mixture comprises 19.90 wt. % molecular hydrogen, 79.59 wt. % methane, and 0.52 wt. % carbon monoxide, based on the weight of the first mixture.

A second mixture is derived from the first mixture by the pyrolysis. The second mixture comprises 29.82 wt. % molecular hydrogen, 23.89 wt. % methane, 28.47 wt. % acetylene, 7.67 wt. % ethylene, 0.44 wt. % carbon monoxide and 9.71 wt % coke which remains in the pyrolysis reactor, based on the weight of the second mixture. Except for the coke, the second mixture is conducted away from stage 206 via conduit 2065. In stage 208, hydrogen is removed from the second mixture to produce an upgraded second mixture comprising 0.3310 moles of molecular hydrogen, 0.3472 moles of methane, 0.2546 moles of acetylene, 0.0636 moles of ethylene, and 0.0036 moles of carbon monoxide per mole of the upgraded second mixture: this is conducted away from stage 208 via conduit 2081. In weight percents, the upgraded second mixture comprises 4.50 wt. % molecular hydrogen, 37.79 wt. % methane, 44.97 wt. % acetylene, 12.11 wt. % ethylene, and 0.69 wt. % carbon monoxide, based on the weight of the upgraded second mixture. A recycle stream comprising ethylene and carbon monoxide is conducted via conduit 2121 to mixer 209, where it is combined with the upgraded second mixture to produce a third mixture, which is conducted to acetylene converter stage 210 via conduit 2086. The third mixture, thus derived from the second mixture by separations and the addition of recycled product, comprises 0.0812 moles of molecular hydrogen, 0.4768 moles of methane, 0.025 moles of acetylene, 0.3633 moles of ethylene, 0.005 moles of carbon monoxide, and 0.0487 moles of ethane per mole of the third mixture; this corresponds to 0.80 wt. % of molecular hydrogen, 37.74 wt. % of methane, 3.22 wt. % ($A_2$) of acetylene, 50.33 wt. % ($A_3$) of ethylene, 0.69 wt. % of carbon monoxide, and 7.23 wt. % of ethane, based on the weight of the third mixture. In stage 210, the third mixture is exposed to a conventional acetylene conversion catalyst comprising Pd at a temperature of 51.5° C. and a pressure of 13.4 bar (absolute) to produce a product comprising 0.054 moles of hydrogen, ≤0.001 moles of acetylene, 0.3960 moles of ethylene, 0.4909 moles of methane, 0.0540 moles of ethane, and 0.0051 moles of carbon monoxide per mole of the product; which corresponds to 0.52 wt. % of molecular hydrogen, 37.74 wt. % of methane, 0.0 wt. % ($A_5$) of acetylene, 50.33 wt. % ($A_6$) of ethylene, 0.69 wt. % of carbon monoxide, and 7.23 wt. % of ethane based on the weight of the product. The acetylene conversion is selective for ethylene, with $A_6 \geq A_3$, $A_5 < A_2$, and a selectivity ratio $[(A_6-A_3)/(A_2-A_5)]=0.915$. The product is divided in stage 212 into first and second portions, the first portion (approx. 7.2 wt. %) being conducted away from the process and the second portion (about 92.8 wt. %) being recycled to stage 209 via conduit 2121, the weight percents being based on the weight of the product. The example demonstrates that high temperature thermal pyrolysis of a hydrocarbon and an oxygenate produce an amount of carbon monoxide sufficient to selectively hydrogenate the acetylene produced by the pyrolysis without utilizing a source of carbon monoxide external to the process.

While the illustrative embodiments disclosed herein have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all inventive features which reside herein, including all features which would be treated as equivalents thereof by those skilled in the art to which this disclosure pertains.

The invention claimed is:

1. A hydrocarbon conversion process, comprising:
   (a) providing a first mixture comprising hydrocarbon and ≥10 wt. % of $CO_2$ based on the weight of the first mixture;
   (b) exposing the first mixture to high severity thermal pyrolysis conditions including a temperature in the range of from $1.45 \times 10^{3}$° C. to $2.20 \times 10^{3}$° C., a total pressure in the range of from 2 bar (absolute) to 10 bar (absolute), and a residence time $\leq 5.0 \times 10^{-3}$ second, in a first region to form a second mixture, the second mixture having a CO:acetylene molar ratio in the range of $2.5 \times 10^{-3}$ to 3.0, a $CO_2$:acetylene molar ratio ≤0.01, and comprising ≥1.0 wt. % $C_2$ unsaturates based on the weight of the second mixture;
   (c) transferring at least a portion of the second mixture, as a transferred mixture, to at least one acetylene converter; and
   (d) catalytically converting at least a portion of the transferred mixture in the acetylene convertor to produce a product;
   wherein,
   the transferred mixture has a CO:acetylene molar ratio in the range of 0.01-1.5 and comprises $A_2$ wt % acetylene and $A_3$ wt % ethylene based on the weight of the transferred mixture,
   the catalytic converting is carried out in the presence of an a catalyst comprising ≥0.1 wt. % of one or more of Pt, Pd, and Ni, and
   the product comprises $A_5$ wt. % of acetylene and $A_6$ wt. % of ethylene based on the weight of the product wherein $A_6 \geq A_3$, $A_5 < A_2$, and $(A_6-A_3)/(A_2-A_5) \geq 0.50$.

2. The process of claim 1, wherein the catalytic acetylene conversion is conducted at least partially in the vapor or liquid phase and wherein $(A_6-A_3)/(A_2-A_5) \geq 0.70$.

3. The process of claim 1, wherein
   (i) the first mixture further comprises molecular hydrogen, and
   (ii) the hydrocarbon of the first mixture comprises methane.

4. The process of claim 1, further comprising exothermically reacting a fourth mixture in a second region to produce a fifth mixture, the first and second regions being at least partially coextensive, and conducting the fifth mixture away from the second region; wherein
   (i) the fourth mixture comprises (i) hydrocarbon and/or hydrogen and (ii) oxidant,
   (ii) the fifth mixture comprises water and/or carbon dioxide, and
   (iii) the exposing of the first mixture and the reacting of the fourth mixture occur at substantially different times.

5. The process of claim 4, wherein
   (i) the hydrocarbon conversion process is continuous or semi-continuous,
   (ii) at least a portion of the fifth mixture is conducted away from the second region before the exposing of the first mixture in the first region, and
   (iii) the exposure temperature in the first region results at least in part from the heat generated during the reacting of the fourth mixture in the second region.

6. The process of claim 4, further comprising at least one of:
   (i) separating from the fifth mixture a byproduct comprising oxygenate and utilizing least a portion of the separated byproduct to produce the first and/or fourth mixtures or
   (ii) separating from the second mixture a second byproduct comprising hydrocarbon and hydrogen and utilizing at least a portion of the separated second byproduct to produce at least one of the first, third, or fourth mixtures.

7. The process of claim 1, wherein the transferred mixture comprises a third mixture, the process further comprising exposing at least a portion of the second mixture to a temperature <100.0° C.; and separating from the second mixture, prior to transferring the at least a portion of the second mixture, one or more of coke, heteroatom species, or saturated hydrocarbons to form the third mixture.

8. The process of claim 1, wherein the acetylene conversion catalyst is a selectivated acetylene conversion catalyst, the catalyst being selectivated by at least a portion of the transferred mixture's carbon monoxide.

9. The process of claim 1, wherein (i) the first mixture has a hydrogen content in the range of 6.0 wt. % to 25.0 wt. % and/or (ii) the first mixture further comprises $\geq 15.0$ wt. % molecular hydrogen based on the weight of the first mixture.

10. The process of claim 1, further comprising compressing the second mixture.

11. The process of claim 1, further comprising contacting the second mixture with a fluid having a pH >7.0.

12. The process of claim 1, further comprising separating ethylene from the product and enriching at least a portion of the transferred mixture with separated ethylene to produce a third mixture.

13. The process of claim 1, wherein (i) the second mixture comprises $5.0 \times 10^2$ ppmm to $1.0 \times 10^4$ ppmm of carbon monoxide per mole of the second mixture and/or (ii) the second mixture has a carbon monoxide to acetylene molar ratio in the range of $2.5 \times 10^{-3}$ to 1.0.

14. The process of claim 1, wherein the transferred mixture has a carbon monoxide:acetylene molar ratio in the range of 0.04 to 0.50 and a molecular hydrogen:acetylene molar ratio in the range of 1.0 to 50.0, the transferred mixture comprising (i) $\geq 2.0$ wt. % $C_2$ unsaturates based on the weight of the third mixture and (ii) $1.0 \times 10^3$ ppmm to $2.5 \times 10^4$ ppmm of carbon monoxide per mole of the third mixture.

15. The process of claim 1, wherein the transferred mixture has a carbon monoxide:acetylene molar ratio in the range of $3.5 \times 10^{-3}$ to 0.20 and comprises $2.0 \times 10^2$ ppmm to $1.0 \times 10^4$ ppmm of carbon monoxide per mole of the second mixture.

16. The process of claim 1, wherein the second mixture has a carbon monoxide:acetylene molar ratio in the range of 0.005 to 0.050.

17. The process of claim 1, further comprising polymerizing at least a portion of the ethylene in the product.

18. The process of claim 17, further comprising separating at least a portion of the carbon monoxide in the product before the polymerizing.

19. The polymer product of claim 17.

20. A hydrocarbon conversion process, comprising:
   (a) mixing hydrocarbon and $CO_2$ to provide a first mixture wherein the first mixture comprises $\geq 1$ wt. % $CO_2$ based on the weight of the first mixture;
   (b) exposing the first mixture to high severity thermal pyrolysis conditions including a temperature in the range of from $1.45 \times 10^{3}$° C. to $2.20 \times 10^{3}$° C., a total pressure in the range of from 2 bar (absolute) to 10 bar (absolute), and a residence time $\leq 5.0 \times 10^{-3}$ second, to form a second mixture having a CO:acetylene molar ratio in the range of 0.04 to 0.50 and a $CO_2$:acetylene molar ratio $\leq 0.01$; and
   (c) catalytically converting at least a portion of the second mixture in the presence of an acetylene conversion catalyst to form a product;
   wherein,
   the second mixture comprises $\geq 1.0$ wt. % $C_2$ unsaturates, $A_1$ wt. % of saturated hydrocarbon, $A_2$ wt. % of acetylene, and $A_3$ wt. % of ethylene based on the weight of the second mixture,
   the acetylene conversion catalyst comprises $\geq 0.1$ wt. % of one or more of Pt, Pd, and Ni,
   the product comprises $A_4$ wt. % of saturated hydrocarbon, $A_5$ wt. % of acetylene, and $A_6$ wt. % of ethylene based on the weight of the product, wherein (i) $A_6 \geq A_3$, (ii) $A_5 < A_2$, (iii) $(A_6-A_3)/(A_2-A_5) \geq 0.70$, and
   the conversion catalyst is selectivated by at least a portion of the second mixture's carbon monoxide.

21. A hydrocarbon conversion process, comprising:
   (a) mixing hydrocarbon and $CO_2$ to provide a first mixture comprising $\geq 10$ wt. % $CO_2$ based on the weight of the first mixture;
   (b) exposing the first mixture to high severity thermal pyrolysis conditions including a temperature in the range of from $1.45 \times 10^{3}$° C. to $2.20 \times 10^{3}$° C., a total pressure in the range of from 2 bar (absolute) to 10 bar (absolute), and a residence time $\leq 5.0 \times 10^{-3}$ second, to form a second mixture having a CO:acetylene molar ratio in the range of $2.5 \times 10^{-3}$ to 3.0, a $CO_2$:acetylene molar ratio $\leq 0.1$, and comprising $\geq 1.0$ wt. % $C_2$ unsaturates based on the weight of the second mixture;
   (c) deriving a third mixture from the second mixture the third mixture having a CO:acetylene molar ratio in the range of 0.04 to 0.50; and (d) catalytically converting at least a portion of the third mixture in the presence of an acetylene conversion catalyst to form a product;

wherein, the third mixture comprises $\geq 1.0$ wt. % $C_2$ unsaturates, $A_1$ wt. % of saturated hydrocarbon, $A_2$ wt. % of acetylene, and $A_3$ wt. % of ethylene based on the weight of the third mixture, the acetylene conversion catalyst comprises $\geq 0.1$ wt. % of one or more of Pt, Pd, and Ni, the product comprising $A_4$ wt. % of saturated hydrocarbon, $A_5$ wt. % of acetylene, and $A_6$ wt. % of ethylene based on the weight of the product, wherein (i) $A_1 \geq 1.0$, ii) $A_2 \geq 1.0$, iii) $A_6 \geq A_3$, (iv) $A_5 < A_2$, (v) $(A_6-A_3)/(A_2-A_5) \geq 0.70$, and the acetylene conversion catalyst is selectivated by at least a portion of the third mixture's carbon monoxide.

* * * * *